(12) United States Patent
Yong et al.

(10) Patent No.: US 6,750,248 B2
(45) Date of Patent: Jun. 15, 2004

(54) METHODS FOR PREPARING AN ESTROGENIC PREPARATION AND ISOLATED ESTROGENIC COMPOUNDS FROM A PLANT AND USES THEREOF

(75) Inventors: Eu Leong Yong, Singapore (SG); Sook Peng Yap, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 10/289,079

(22) Filed: Nov. 5, 2002

(65) Prior Publication Data

US 2003/0170292 A1 Sep. 11, 2003

Related U.S. Application Data

(60) Provisional application No. 60/331,183, filed on Nov. 9, 2001.

(51) Int. Cl.$^7$ .............................................. A61K 31/35
(52) U.S. Cl. ...................... 514/456; 549/401; 549/403; 424/725
(58) Field of Search ........................ 514/456; 549/401, 549/403; 424/725

(56) References Cited

U.S. PATENT DOCUMENTS

| | | | |
|---|---|---|---|
| 5,874,084 A | 2/1999 | Yng-Wong | .................. 424/740 |
| 6,071,883 A | 6/2000 | Chen et al. | ..................... 514/25 |
| 6,123,944 A | 9/2000 | Chen et al. | .................. 424/725 |
| 6,238,707 B1 | 5/2001 | Chun | .......................... 424/725 |

FOREIGN PATENT DOCUMENTS

| | | | | |
|---|---|---|---|---|
| WO | 9947137 | 3/1999 | .......... | A61K/31/35 |
| WO | 0101996 | 6/2000 | ........... | A61P/19/10 |

OTHER PUBLICATIONS

Barkhem, Tomas et al. (1998) "Differential Response of Estrogen Receptor α and Estrogen Receptor β to Partial Estrogen Agonists/Antagonists". *Molecular Pharmacology.* vol. 54: pp. 105–112.

Brzozowski, Andrzej M. et al. (1997) "Molecular Basis of Agonism and Antagonism in the Oestrogen Receptor". *Nature.* vol. 389: pp. 753–758.

Chen, Chien–Chih et al. (1996) "New Prenylflavones from the Leaves of *Epimedium Sagittatum*". *Journal of Natural Products.* vol. 59(4): pp. 412–414.

Conneely, Orla M. (2001) "Perspective: Female Steroid Hormone Action". *Endocrinology* vol. 142(6): pp. 2194–2199.

Diel, Patrick et al. (2001) "Molecular Identification of Potential Selective Estrogen Receptor Modulator (SERM) Like Properties of Phytoestrogens in the Human Breast Cancer Cell Line MCF–7". *Planta Med.* vol. 67: pp. 510–514.

Glazier, M. Gina et al. (2001) "A Review of the Evidence for the Use of Phytoestrogens as a Replacement for Traditional Estrogen Replacement Therapy". *Arch Intern Med.* vol. 161: pp. 1161–1172.

Gustafsson, Jan–Åke et al. (2000) "Estrogen receptor β in the Breast: Role in Estrogen Responsiveness and Development of Breast Cancer". *Journal of Steroid Biochemistry & Molecular Biology.* vol. 74: pp. 245–248.

Horvath, Lisa G. et al. (2001) "Frequent Loss of Estrogen Receptor–β Expression in Prostate Cancer". *Cancer Research.* vol. 61: pp. 5331–5335.

Kuroda, Minpei et al. (2000) "Flavonol Glycosides from *Epimedium Sagittatum* and Their Neurite Outgrowth Activity on PC12h Cells". *Planta Med.* vol. 66: pp. 575–577.

Kurzer, Mindy S. et al. (1997) "Dietary Phytoestrogens". *Annu. Rev. Nutr.* vol. 17: pp. 353–381.

Lee, H. P. et al. (1991) "Dietary Effects on Breast–Cancer Risk in Singapore". *The Lancet.* vol. 337: pp. 1197–1200.

Lee, Mi–Kyeong et al. (1995) "Antihepatotoxic Activity of Icariin, a Major Constituent of *Epimedium Koreanum*". *Planta Med.* vol. 61: pp. 523–526.

Lee, Sang–Jun et al. (2000) "Structure–Activity Relationship of Dietary Flavonoids for Inhibitory Activity of Mouse Brain Monoamine Oxidase (MAO) in vitro". *Food Sci. Biotechnol.* vol. 9(5): pp. 304–307.

Liang, H. –R. et al. (1997) "Characterization of Flavonoids in Extracts from Four Species of Epimedium by Micellar Electrokinetic Capillary Chromatography with Diode–Array Detection". *Journal of Chromatographic Science.* vol. 35: pp. 117–125.

Liang, H. –R. et al. (1997) "Isolation and Immunomodulatory Effect of Flavonol Glycosides from *Epimedium Hunanense*". *Planta Medica.* vol. 63: pp. 316–319.

Milligan, S.R. et al. (2000) "The Endocrine Activities of 8–Prenylnaringenin and Related Hop (*Humulus Lupulus* L.) Flavonoids". *The Journal of Clinical Endocrinology & Metabolism.* vol. 85(12): pp. 4912–4915.

(List continued on next page.)

*Primary Examiner*—Amelia Owens
(74) *Attorney, Agent, or Firm*—Klarquist Sparkman, LLP

(57) ABSTRACT

Methods for preparing an estrogenic preparation and isolating estrogenic compounds from a plant, such as an Epimedium plant, are provided. Also provided are estrogenic compounds from Epimedium plant that have been isolated and characterized, and methods for their use in modulating estrogen receptors and in treating conditions mediated by estrogen receptors, such as menopause and estrogen-dependent cancers. Also provided are preparations from Epimedium that are enriched for estrogenic compounds, and methods for their use in modulating estrogen receptors and preventing and treating conditions that are mediated by estrogen receptors.

51 Claims, No Drawings

OTHER PUBLICATIONS

Omoto, Yoko et al. (2001) "Expression, Function, and Clinical Implications of the Estrogen Receptor β in Human Lung Cancers". *Biochemical and Biophysical Research Communications.* vol. 285(2): pp. 340–347.

Österlund, Marie K. et al. (2000) "Estrogen Receptor β (ERβ) Messenger Ribonucleic Acid (mRNA) Expression Within the Human Forebrain: Distinct Distribution Pattern to ERα mRNA". *The Journal of Clinical Endocrinology &.*

Journel of Chromatographic Science, vol. 35, No. 3, 1997, pp. 117–125, H.-R. Liang et al, "Characterization of flavonoids in extracts from four species of Epimedium by micellar electrokinetic capillary chromatography with diode–array detection." See entire document.

Planta Medica, vol. 62, No. 2, 1996, pp. 150–153, H. Miura et al, "Effect of crude fractions of *Psoralea corylifolia* seed extract on bone calcification." See entire document.

Archives of Pharm. Research, vol. 24, No. 3, 2001, pp. 211–213, W. Mar et al, "Cytotoxic constituents of *Psoralea corylifolia.*" See entire document.

Journel of Ethnopharmacology, vol. 18, No. 1, 1986, pp. 21–31, M. Nisa et al, "Effect of *Cuscuta chinensis* water extract on 7, 12–dimethylbenz[α]anthracene–induced skin papillomas and carcinomas in mice." See entire document.

Chemical Abstract 86:13826 & Rastitel'nye Resursy, vol. 12, No. 4, 1976, pp. 515–525, A.G. Kurmukov et al, "Phytoestrogens from plants of Central Asia." See abstract.

Metabolite vol. 85(10): pp. 3840–3846.

Paech, Kolja et al. (1997) "Differential Ligand Activation of Estrogen Receptors ERα and ERβ at AP1 Sites". *Science.* vol. 277: pp. 1508–1510.

Pettersson, Katarina et al. (2001) "Role of Estrogen Beta in Estrogen Action". *annu. Rev. Physiol.* vol. 63: pp. 165–192.

The Pharmacopoeia Commission of People's Republic of China. (1997) "Pharmacopoeia of the People's Republic of China". (English Edition) Chemical Industry Press. Beijing, China. vol. 1: pp. 93–94; Appendix V: A–26–A27; Appendix VI: A–30–A31.

Pike, Ashley C.W. et al. (1999) "Structure of the Ligand–Binding Domain of Oestrogen Receptor Beta in the Presence of a Partial Agonist and a Full Antagonist". *The EMBO Journal.* vol. 18(17): pp. 4608–4618.

Roger, Pascal et al. (2001) "Decreased Expression of Estrogen Receptor β Protein in Proliferative Preinvasive Mammary Tumors". *Cancer Research.* vol. 61: pp. 2537–2541.

Rosenberg Zand, Rachel S. et al. (2000) "Steroid Hormone Activity of Flavonoids and Related Compounds". *Breast Cancer Research and Treatment.* vol. 62: pp. 35–49.

Setchell, Kenneth (1998) "Phytoestrogens: The Biochemistry, Physiology, and Implications for Human Health of Soy Isoflavones". *Am J Clin Nutr.* vol. 68(suppl): 1333S–1346S.

Tham, Doris M. et al. (1988) "Potential Health Benefits of Dietary Phytoestrogens: A Review of the Clinical, Epidemiological, and Mechanistic Evidence". *Journal of Clinical Endocrinology and Metabolism.* vol. 83(7): pp. 2223–2235.

Wang, Ling et al. (2001) "Morphological Abnormalities in the Brains of Estrogen Receptor β Knockout Mice". *PNAS.* vol. 98(5): pp. 2792–2796.

Weihua, Zhang et al. (2001) "A Role for Estrogen Receptor β in the Regulation of Growth of the Ventral Prostate". *PNAS.* vol. 98(11): pp. 6330–6335.

Zava, David T. et al. (1998) "Estrogen and Progestin Bioactivity of Foods, Herbs, and Spices". *P.S.E.B.M.* vol. 217: pp. 369–378.

METHODS FOR PREPARING AN ESTROGENIC PREPARATION AND ISOLATED ESTROGENIC COMPOUNDS FROM A PLANT AND USES THEREOF

CROSS-REFERENCE TO RELATED APPLICATIONS

This application claims the benefit of U.S. provisional patent application serial No. 60/331,183 filed Nov. 9, 2001, which is incorporated herein by reference in its entirety.

FIELD OF THE INVENTION

The current invention concerns methods of preparing an estrogenic preparation and isolating an estrogenic compound from a plant, such as an Epimedium plant, and uses thereof for selectively modulating the function of estrogen receptors.

BACKGROUND OF THE INVENTION

There is an ever-increasing interest in herbal or natural-source remedies or medications. Many individuals would rather use such products than conventional pharmaceutical preparations. Additionally, medicinal substances derived from natural products can provide commercial or industrial opportunities for local populations in areas where medicinal plants grow or are cultivated. Moreover, compounds identified as the active ingredients in natural products form an important basis for pharmaceutical research.

Estrogens are steroid hormones that regulate physiological processes such as the growth, differentiation, and functioning of many target tissues by regulating the expression of genes under control of estrogen-responsive elements. Tissues that express estrogen receptors include tissues of the female and male reproductive systems such as the mammary gland, uterus, vagina, ovary, testes, epididymis, and prostate (For reviews see: Pettersson, et al., 2001; Conneely, 2001). Estrogens have been increasingly shown to have important regulatory roles in the central nervous system and cardiovascular system and in physiological processes such as the maintenance of bone, lipid and fat metabolism, and atherosclerosis formation. Of the several physiological estrogens in women, 17-beta-estradiol (hereinafter referred to as "estradiol") is the most potent.

"Phytoestrogens" are a broad group of plant-derived compounds of non-steroidal structure that can behave as estrogen mimics (For reviews: Kurzer, et al., 1997; Zava, et al., 1998; Setchell, 1998; Tham, et al., 1998). A typical feature of the chemical structure of phytoestrogens is the presence of a phenolic ring that, with few exceptions, is a prerequisite for binding to the estrogen receptor. Phytoestrogenic substances have been demonstrated to have estrogenic or anti-estrogenic activity and epidemiological data suggests that these substances may be useful for treatment of a variety of health problems that are correlated with estrogenic deficiency, including: premature ovarian failure; menopausal syndromes; osteoporosis; menstrual irregularities; pre-menstrual syndrome; cardiovascular disease; atherosclerosis, coronary artery disease and strokes; and cancer. These potential health benefits are consistent with epidemiological evidence that rates of heart disease, hormone-dependent cancers, osteoporotic fractures and menopausal symptoms are more favorable among populations that consume plant-based diets, especially among cultures with diets rich in soy products.

The biological effects of estrogens are mediated via estrogen receptors (ER), of which there are at least two types, i.e. ER-alpha and ER-beta (Pettersson, et al., 2001; Conneely, 2001). Estrogens are retained in target cells by the estrogen receptors (ERs). The ERs belong to the steroid-receptor superfamily of nuclear transcription factors, whose members include receptors for progesterone (PR), glucocorticoids (GR) and androgens (AR). The ERs, in common with other members of the steroid-receptor superfamily, are organized into domains that are responsible for specific functions. The N-terminal transactivation domain has a ligand-independent activation function. The DNA-binding domain (DBD) enables the receptor to bind to its cognate target site consisting of an inverted repeat of two half-sites with the consensus motif AGGTCA (or closely related sequences) spaced by 3 basepairs and referred to as an estrogen response element (ERE). The DBDs of ER-alpha and ER-beta share approximately 97% sequence homology but significant differences in amino-acid sequences are found in the N-terminal, and ligand-binding domains. Both ER-alpha and ER-beta bind to EREs in promoter regions of target cells. In addition ERs can regulate AP-1 enhancer elements, by acting on the transcription factors Fos and. Jun. The ligand-binding domain (LBD) also harbors a nuclear localization signal as well as sequences necessary for dimerization and transcriptional activation. Upon estrogen binding, ER undergoes a conformational change allowing the receptor to interact with chromatin and to modulate transcription of target genes. Modulation of gene expression leads to changes in the level of expression of corresponding proteins, which in turn bring about the myriad physiological activities associated with estrogens.

Although both ER-alpha and ER-beta bind specifically to the same estrogen response element (ERE), there are important differences in their actions in cellular systems and in their response to agonists and antagonists (Enmark, et al., 1998, Barkhem, et al., 1998). ER-beta requires approximately five- to ten-fold higher concentrations of estradiol than ER-alpha for maximum transactivation activity to occur and ER-beta is only approximately 30% as efficient as ER-alpha in a variety of reporter gene systems. The anti-estrogen tamoxifen is a mixed agonist/antagonist for ER-alpha but is a pure antagonist for ER-beta. ER-alpha and ER-beta can form functional DNA-binding heterodimeric complexes, and in these complexes ER-beta appears to be the dominant partner, given that activity is repressed at low concentrations of estradiol and in the presence of tamoxifen. Notably, ER-alpha and ER-beta have opposite effects at AP-1 and SP-1 sites (Paech, et al., 1997), in the presence of both agonists and antagonists. ER-alpha and ER-beta also bind to the same ligands with different affinity. In addition, after binding to estrogens and anti-estrogens, ER-alpha and ER-beta use different enhancer elements such as estrogen responsive element and AP1 sites in promoter regions of genes. Taken together, these studies suggest that ER-alpha and ER-beta may activate different downstream effects.

There are substantial differences in the distribution of ER-alpha and ER-beta in estrogen responsive tissues. ER-beta is expressed in many human tissues including the central nervous system, the cardiovascular system, the immune system, the urogenital tract, the gastrointestinal tract, the kidneys and the lungs (Omoto, et al., 2001). In contrast ER-alpha seems to predominate in reproductive tissues such as the uterus and breast, although smaller amounts of ER-beta are also present in these tissues. It is possible that ER-beta is the more widely expressed estrogen receptor in the body.

In tissues where both ER-alpha and ER-beta are co-expressed, it has been found in many cases that ER-beta opposes the actions of ER-alpha.

Phytochemicals and Phytoestrogens

Phytoestrogens may have partial estrogenic and anti-estrogenic activity due to their competition with endogenous estradiol for estrogen receptors (For reviews: Kurzer, et al., 1997; Zava, et al., 1998; Setchell, 1998; Tham, et al., 1998). The majority of phytoestrogens found in plants (including herbs and legumes) can be categorized into two primary classes: flavonoids and lignans. These substances have a structural similarity to the estrogens, estradiol and diethylstilbesterol, especially in relation to their —OH groups.

Flavonoids represent a family of phytochemicals with disparate functions, including: deterring herbivores, acting as antibacterial/antifungal agents and stimulating the formation of symbiotic relationships with nitrogen-fixing bacteria. The family of flavonoids is often subclassified on the basis of structural features into: flavones, isoflavones or coumestans. Isoflavones make up the most common form of phytoestrogens. Typically, phytoestrogens exhibit weak estrogenic activity, i.e. on the order of 100- to 1000-fold weaker activity compared to estradiol, but since these compounds may be present in the body in concentrations of 100-fold higher than endogenous estrogens, they may be present in the body at levels sufficient to compete with endogenous estrogen or compensate for estrogen deficiency. Two isoflavonoids, genistein and daidzein, found in soybean tissue have been described as being 100–1000 times less active than estradiol, and are therefore effective as agonists of ER-alpha at 100–1000 times greater concentrations.

Flavones with estrogenic activity are uncommon and known examples include 8-prenylnaringenin and 6-prenylnarigenin from hops, 6-hydroxyflavone and luteolin. In particular the prenylated flavone, 8-prenylnaringenin, isolated from hops has been described to be a potent phytoestrogen with an activity which is greater than other established plant estrogens (Milligan, et al., 1999).

Phytoestrogens may have favourable effects on the risk of cardiovascular disease and are thought to be hypocholesterolemic, anticarcinogenic, antiproliferative, antiosteoporotic, and hormone altering. These health benefits may be attributable to a variety of mechanisms, including ER action.

Epimedium Herb

Epimedium herb (Yin Yang Huo) is a traditional Chinese herb consisting of the dried aerial part of *E. sagitatum* (Sieb. et Zucc.), *E. koreanum* Nakai (Fam.Berberidaceae), *E. pubescens* Maxm., *E. wushanense* T. S. Ying, or *E. brevicorum* Maxim or mixtures thereof. The herb is listed in Pharmacopoeia of the People's Republic of China (1997) as having action to "reinforce the kidney yang, strengthen tendons and bones, and relieve rheumatic conditions" and indicated "for impotence, seminal emission, weakness of the limbs, rheumatoid arthralgia with numbness and muscle contracture, and climacteric hypertension".

Several compounds including flavones and isoflavones have been isolated from Epimedium herb. These compounds have been found to have disparate physiological activities. Compounds isolated from the aerial parts of Epimedium herb include icariin, phenooxychromones, flavonoids, chrysoeriol, quercetin, apigenin, apigenin 7,4'-dimethyl ether, kaempferol, luteolin, and brevicornin (Liang, et al., 1997a,).

Luteolin, a flavone, has been described as having estrogenic activity with a relative potency of 58% compared to genistein (Rosenberg Zand, et al., 2000). Apigenin and quercetin have also been described as being estrogenic with relative potencies of 16% and 10% respectively compared to genistein.

Other flavonoids and flavanol glycosides described in Epimedium herb include epimedokoreanoside I, epimedin B and C, beta-anhydroicaritin, tricin, and Baohuoside III, V, and VI, some of which flavonol glycosides were reported to have immuno-modulatory activity (Liang, et al., 1997b).

Chen et al. (1996) described the isolation of 5 new prenyflavones, Yin Yang Huo A, B, C, D, and E, some of which (i.e. Yin Yang Huo A and B) were described as having significant anti-platelet activity.

A flavone analogue, Baihuoside I, isolated from Epimedium herb was described as being an anti-rejection agent, effective at prolonging mouse heart allograft survival (U.S. Pat. No. 6,071,883: Chen et al., 2000). Assessment of the mice for appearance, behaviour, biochemistry, hematology and histology revealed no side effects even at the intraperitoneal dose of 32 mg/kg/day for 14 days.

Icariin-containing preparations have been isolated from aerial parts of plants of the genus Epimedium (U.S. Pat. No. 6,123,944: Chen et al., 2000). These icariin-containing preparations were stated to be effective in treating osteoporosis. Bone phosphorus and calcium contents, bone mineral density and the femur strength of treated ovariectomized rats were increased significantly compared to control groups.

Icariin compounds have been described as displaying anti-hepatotoxic activity in cultured rat hepatocytes (Lee et al., 1995).

Methanol extract of *E. sagitatum* was stated to show neurite outgrowth activity on cultured PC12H cells. Bioassay guided fractionation yielded six prenylated flavonol glycosides, ikarisiside A, icarisid II, epimedoside A, icariin, epimedin B and epimedokoreanosid-1 as the active ingredients (Kuroda, 2000).

Complex mixtures of herbs comprising *Epimedium grandiforum* have been described as a method to treat hot flushes (U.S. Pat. No. 5,847,084, Yng Wong, 1999; U.S. Pat. No. 6,238,707, Chun, 2001).

Many women perceive prescription estrogens as being unnatural and there is an increasing interest in the use of plant-derived estrogens for treatment of post-menopausal problems and other conditions associated with estrogen receptors or estrogen-deficiency (Glazier, et al., 2001). Thus, there is a need to identify naturally occurring compounds that interact with and activate ER, especially ER-beta. Natural estrogen receptor activating compounds are needed for the development of therapeutic compositions and/or neutraceutical applications. Pure chemical entities, isolated and purified from herbs can also be developed as pharmaceutical agents.

SUMMARY OF INVENTION

The present invention provides methods of preparing an estrogenic preparation and isolating an estrogenic compound from a plant, such as an Epimedium plant, and the use of the estrogenic preparation or the isolated estrogenic compound in modulating an estrogen receptor.

In one aspect, the invention provides a method for modulating an estrogen receptor comprising contacting said estrogen receptor with a compound having the formula I:

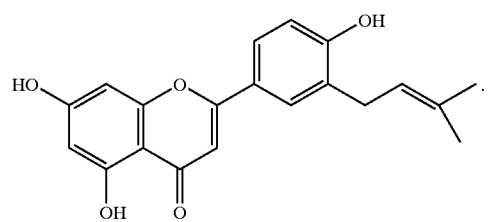

In a further aspect, the invention provides a compound having the formula II:

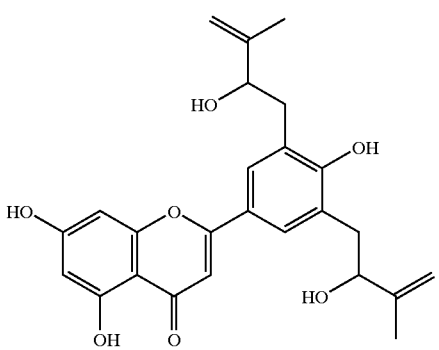

It will be seen that formula II has two chiral carbon atoms and that the invention extends to all stereoisomers, diastereomers, enantiomers and racemates of formula II.

In a further aspect, the invention provides a compound having the formula III:

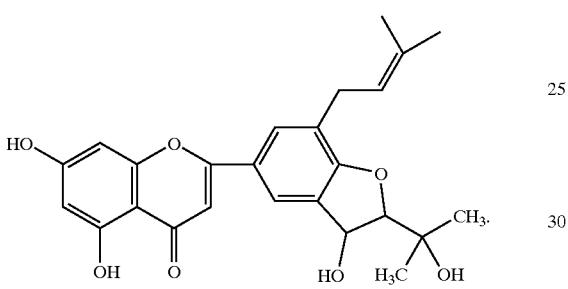

It will be seen that formula III has two chiral carbon atoms and that the invention extends to all stereoisomers, diastereomers, enantiomers and racemates of formula III.

In a further aspect, the invention provides a method for modulating an estrogen receptor comprising contacting an estrogen receptor with a compound having the formula III.

In a further aspect, the invention provides a pharmaceutical composition, nutritional supplement, food product or beverage, comprising a compound having the formula III.

In a further aspect, the invention provides a commerical package comprising a pharmaceutical composition, nutritional supplement, food product or beverage, comprising a compound having the formula III together with instructions for use in treating a condition mediated by an estrogen receptor.

In a further aspect, the invention provides a method for preparing a preparation having estrogenic activity from a plant, said method comprising:
  (a) extracting the plant or a part thereof with a solvent to obtain an extract;
  (b) fractionating said extract to obtain a plurality of fractions;
  (c) assaying estrogen receptor agonist activity in the fractions from (b); and
  (d) collecting a fraction from (c) that is enriched for estrogen receptor agonist activity by about 2-fold or more relative to said extract.

In a further aspect, the invention provides a preparation prepared according to the method described herein from a plant selected from the group consisting of *Dioscorea opposita; Anemarrhena asphodeloides; Cuscuta chinensis*; and *Psoralea corylifoloa*.

In a further aspect, the invention provides a preparation having estrogenic activity obtained from an Epimedium plant, wherein said preparation comprises between about 0.002% to 99.9% by weight of a compound having the formula III. The invention further provides a pharmaceutical composition, nutritional supplement, food product or beverage comprising such a preparation. The invention further provides a commercial package comprising such a preparation together with instructions for use for modulating an estrogen receptor.

In a further aspect, the invention provides a method for preventing or treating a condition mediated by an estrogen receptor in a subject comprising administering to a subject in need thereof a therapeutically effective amount of:
  (i) a compound of the formula:

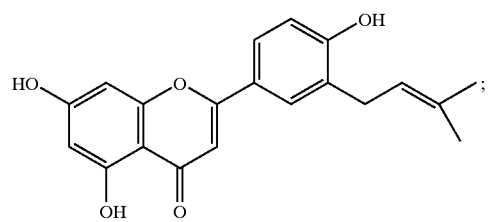

(ii) a compound of the formula:

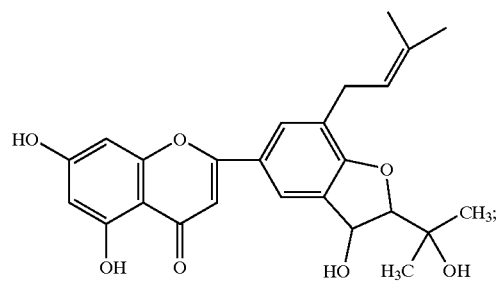

(iii) a mixture of said compound in (i) and said compound in (ii); or
  (iv) a preparation having estrogenic activity obtained from an Epimedium plant, wherein said preparation comprises between about 0.002% to 99.9% of a compound of the formula:

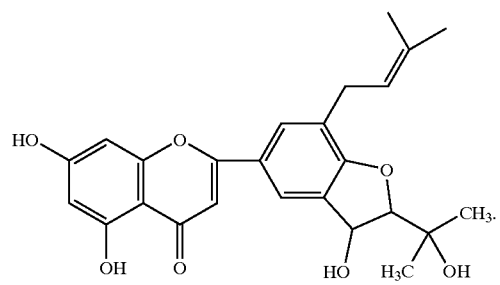

DETAILED DESCRIPTION

Methods for preparing estrogenic preparations and isolating estrogenic compounds from a plant, such as an Epimedium plant, are herein described.

By "estrogenic" we mean having the property of being able to stimulate or activate estrogen receptors, including homodimers of ER-alpha and ER-beta subunits and heterodimers comprised of ER-alpha and ER-beta subunits. Thus, "estrogenic extract", "estrogenic preparation" and "estrogenic compound" refer to extracts, preparations or compounds, respectively, that are capable of stimulating estrogen receptors. Estrogenic preparations and compounds may be described herein as having "estrogen receptor agonist activity" or "estrogenic activity", particularly in the context of describing results of assays and in characterizing fractions obtained by the methods herein described. An estrogenic compound may also be described herein as being an "estrogen receptor agonist".

In the context of the present invention, the expression "Epimedium plant" means a plant (or part(s) thereof) of the genus Epimedium and includes Epimedium herb (i.e. the traditional Chinese herb, Epimedium herb or "Yinyanghuo") and mixtures of plants of different Epimedium species.

"Crude extract" of a plant refers to the extract obtained by extracting the plant or part(s) thereof with a solvent, without fractionating the extract to enrich for estrogenic compounds. In the present context, the expression "ES extract" means an estrogenic extract of Epimedium plant, and "ES crude extract" means estrogenic crude extract of Epimedium plant.

A compound that shows stronger agonist activity with a receptor type over others may be described as being "selective" for that receptor. For example, a compound that shows stronger agonist activity with one of the ER subtypes, ER-alpha and ER-beta, over the other may be described as being "selective" for that subtype.

The terms "alpha estrogen receptor" and "ER-alpha" refer to homodimers comprised of ER-alpha subunits. The terms "beta estrogen receptor" and "ER-beta" refer to homodimers comprised of ER-beta subunits. It is expected that a compound that binds to ER-alpha and ER-beta will also bind to a heterodimeric estrogen receptor, ER-alpha/ER-beta, comprised of alpha and beta estrogen receptor subunits.

The estrogenic preparations and isolated estrogenic compounds from a plant, such as an Epimedium plant, are useful for modulating estrogen receptors. Therefore, the estrogenic preparations and isolated estrogenic compounds may be useful for treating conditions that are mediated by estrogen receptors. The expression "condition mediated by an estrogen receptor" includes any condition that may benefit from administration of an endogenous estrogen receptor agonist to a subject. Such conditions include but are not limited to conditions that arise as a result of insufficient or deficient estrogen supply in a subject, for example conditions associated with menopause.

As used herein, the term "modulate" means to alter the activity of a biologically active protein, such as the estrogen receptor protein. By "modulating an estrogen receptor protein", we mean altering its biological activities, such as its binding to estrogen response elements (ERE) in the chromatin. Modulation of a biologically active protein can stimulate (i.e. activate) or inhibit activity of the protein.

Methods

Methods are described herein for preparing estrogenic preparations and isolated estrogenic compounds from a plant, such as an Epimedium plant. In one embodiment, these methods can be used to identify and isolate estrogenic compounds that are selective for a particular ER subtype, i.e. ER-alpha or ER-beta.

These methods have been used to isolate two estrogenic compounds from an Epimedium plant, Compound I (having a structure described by formula I, above) and Compound III (having a structure described by formula III, above).

The methods described herein may be used to identify and isolate additional estrogenic compounds from a plant, such as an Epimedium plant, based on their functional property as estrogen receptor agonists.

Estrogenic preparations and isolated estrogenic compounds may be prepared from a plant using any part thereof, including the whole plant, or various parts of the plant, including without limitation: plant cells, tissues, seeds, embryos, leaves, stems, roots, flowers, etc. The method described herein is not limited to the particular part of the plant used to prepare estrogenic preparations and isolated estrogenic compounds. Plants that may be used in the method described herein include without limitation Epimedium plant, *Dioscorea opposita; Anemarrhena asphodeloides; Curculigo orchioides; Cuscuta chinensis; Polygonatum kingianum; Morinda officinalis; Psoralea corylifoloa; Angelica sinensis; Lycium chinense;* and *Radix astragali.*

(i) Assaying Estrogenic Activity

The estrogenic properties of preparations and compounds isolated from a plant, such as an Epimedium plant, can be assayed with cell-based assays to measure the potency and purity and quality of the raw herbs and preparations and isolated compounds derived from it. Examples of cell-based assays for estrogenic activity include: estrogen-reporter gene assays in a cell line transfected with a reporter gene that is under regulatory control of an estrogen response element (ERE); and estrogen-stimulated growth assays, using cell lines whose growth are sensitive to estrogens such as MCF-7 cells. Estrogenic activity may also be assayed with non-cell-based assays, such as ligand-binding assays involving the use of purified receptors in affinity columns.

For example, in a suitable cell-based assay, tissue culture cells (such as Hela cells) are co-transfected (either transiently or stably) with a first plasmid comprising DNA encoding an estrogen receptor and a second plasmid comprising an estrogen-responsive promoter driving a reporter gene (such as luciferase, green fluorescent protein, and CAT (chloramphenical acetyltranferase)), whose transcription is regulated by an estrogen response element; the activity of the estrogenic preparation or a compound isolated therefrom can be assayed by monitoring the expression of reporter gene in test cells versus controls consisting of an estrogen receptor agonist (such as estradiol) and "vehicle" (the solvent in which the estrogenic preparation or isolated compound is dissolved). Other suitable cells for use in this assay include CV1, and COS-7 cells. Other suitable estrogen receptor agonists include estrone, estriol, and diethylstilbesterol.

(ii) Preparation of Estrogenic Preparations and Isolated Estrogenic Compounds from a Plant For the initial extraction of estrogenic compounds from a plant, such as an Epimedium plant, the plant source (a whole plant or a part thereof, such as aerial parts) is extracted with a solvent such as water or alcohol (such as ethanol) or a mixture thereof. Other solvents may be used in the extraction process, including but not limited to acetone, butanol, and methanol. Polar organic solvents are generally preferred. The plant or part thereof may be crushed, ground, mashed, macerated, pulverized, triturated or otherwise broken up before extraction, and doing so may increase the efficiency of extraction. The plant source may be dried or fresh. Plant parts are typically extracted in solvent at a temperature ranging from, for example, room temperature to the boiling point of the solvent, for a period of time ranging from about one hour to about 3 days.

For example, Epimedium crude extract (ES crude extract) can be prepared by mixing crushed aerial parts of Epimedium plant with 100% ethanol and soaked for 5–7 days at 37° C. Other methods such as boiling with water and extraction with varying concentrations of ethanol or methanol are also effective at extracting estrogenic compounds from a plant, such as an Epimedium plant.

Epimedium crude extract (ES crude extract) (100% ethanol) has several properties. It exhibits estrogenic activity but does not have progestogenic, glucocorticoid or androgenic activity at the concentrations tested. Thus ES crude extract can specifically activate the estrogen receptor at concentrations that do not significantly activate other closely-related members of the steroid receptor family. Moreover, ES crude extract can activate estrogen receptors when used at concentrations that do not antagonize estradiol action nor on the action of progestogens, glucocorticoids or androgens.

The ES crude extract thus obtained may be used directly to modulate estrogen receptors, for example as a control in assays for estrogenic activity. Typically, ES crude extract is fractionated to enrich for or isolate estrogenic compounds.

To enrich for estrogenic compounds, ES crude extract can be fractionated. Methods for fractionating estrogenic preparations and isolated estrogenic compounds from a plant, such as an Epimedium plant, may include the following steps or processes: solvent-solvent partitioning, solid-phase fractionations, thin-layer chromatography (TLC), flash chromatography, and high-performance or high pressure liquid chromatography (HPLC).

For example, ES crude extract can be fractionated by loading it on a chromatography column (for example, a bonded phase column such as a Diol solid phase column), eluting with a solvent gradient of increasing or decreasing polarity to obtain a plurality of fractions, some of which may be enriched for estrogen-receptor agonist activity. The fractions thus obtained can be assayed for the presence of estrogenic compounds by assaying for estrogen-receptor agonist activity, as described herein. To determine whether a fraction is selective for ER-alpha or ER-beta, the agonist activity of the fraction for ER-alpha and ER-beta is measured in cells expressing one or the other receptor subtype. Optionally, non-bioactive compounds (such as tannins, chlorophylls) can be removed from ES crude extract before fractionation by loading on a chromatography column packed with matrix, such as polyamide resin, and eluting with a solvent, such as methanol. The eluate thus obtained may be fractionated as described above.

Estrogenic fractions obtained from a first fractionation of ES crude extract may have estrogenic activity that is increased relative to crude extract by 0.5-fold to 10-fold, typically 2-fold to 6-fold (crude extract at 50 $\mu$g/ml exhibits about 55% ER-alpha stimulating activity relative to estradiol at 1 nM). Estrogenic fractions thus obtained, i.e. that are enriched for estrogen receptor agonist activity, may be used directly as estrogenic preparations to modulate estrogen receptor activity. Alternatively, these fractions may be further fractionated to enrich for or isolate estrogenic compounds.

Compound I (MW: 338 Daltons) is a prenylated flavone having a structure described by formula I (above) that may be isolated from an Epimedium plant by: extracting the plant with solvent; fractionating the crude extract thus obtained to obtain a plurality of fractions; assaying the fractions thus obtained for estrogen receptor agonist activity; and collecting one or more fractions that is enriched for estrogen receptor agonist activity relative to said crude extract; further fractionating the estrogen receptor agonist enriched fraction(s), for example by high pressure liquid chromatography (HPLC); and collecting one or more fractions that are enriched for Compound I. The presence of Compound I in a fraction may be determined by negative mass spectrometry (i.e. high resolution electron spray ionization mass spectrum, or HRESIMS) or nuclear magnetic resonance (NMR). Compound I demonstrates estrogenic activity and can activate both ER-alpha and ER-beta. Thus Compound I, or estrogenic preparations enriched for Compound I, may be useful for modulating estrogen receptors.

Compound III (MW: 438 Daltons) is a prenylated flavone having a structure described by formula III (above) which can be isolated from an Epimedium plant and shows specificity for ER-beta. Compound III can be isolated, for example, from estrogenic fractions obtained by fractionating ES extract using solid phase chromatography (for example with Diol and C18 columns), and further fractionating the estrogenic fractions thus obtained to a second HPLC (such as a Luna Phenomenex C18) column using a gradient solvent system, such as an isocratic mobile phase of 43% ACN in $H_2O$ over 20 minutes. Fractions thus obtained may be assayed either to detect the presence of Compound III itself (by NMR or mass spectrophotometry) or by first assaying for ER-beta-selective agonist activity, then confirming the presence of Compound III by NMR or mass spectrophotometry.

Compound III may co-purify with Compound II. Compound II is a prenylated flavone having a structure corresponding to formula II (above). These compounds may be separated from each other by further fractionation, for example by Reverse Phase (RP) Amide HPLC column chromatography using a suitable solvent system (such as a gradient mobile phase from 50% ACN in $H_2O$ to 60% ACN in $H_2O$ over 10 minutes, followed by an isocratic mobile phase of 60% ACN in $H_2O$ for 10 minutes).

If the fractions are subjected to mass spectrometry or NMR analyses, patterns can be found which can be used for quality control purposes. For example, negative mass spectrometric $(M-H)^-$ (HRESIMS) examination may be used to detect whether Compound I (MW 338 Daltons), or Compound II and/or Compound III (both MW 438 Daltons) is present in a fraction. Similarly the gHSQC NMR chemical shifts and COSY gHMBC patterns of ES extracts may be used to standardize and classify the various types of ES extracts. Thus, once an estrogenic compound has been identified and characterized, it is then possible to isolate the compound by detecting its presence in fractions based on known physical properties (by methods such as NMR and Mass spectrophotometry), thereby avoiding the cell-based assay for estrogenic activity during the purification process. However, assays of estrogenic activity of the final product may be used to assure quality control.

Compound I, Compound II and Compound III, respectively, are preferably isolated from other components of Epimedium plant at a purity of between about 70% to 99.9% by weight, and preferably at a purity of at least about 75%, 80%, 85%, 90%, 95%, and 99.9% by weight.

An extract of Epimedium plant, or typically a fraction of such extract, that is enriched for Compound III can be used directly as a Compound III-containing preparation of Epimedium plant. Typically, the preparation will contain Compound III in an amount of at least 0.002% to 99.9% by weight, based on the Epimedium-derived portion of the preparation, and preferably at least 0.01%, even more preferably at least 0.1%, 0.5%, 1%, 2%, 3%, 4%, 5%, 10%, 15%, 20%, 30%, 40%, 50%, 60%, 70%, 80%, 90%, 95%, or 99.9% by weight Compound III, based on the Epimedium plant derived portion of the preparation. Crude extract of Epimedium contains about 0.001% of Compound III.

(iii) Epimedium Plants

Epimedium plants for use in preparing estrogenic preparations and isolated estrogenic compounds as described herein include any Epimedium plant or mixture of Epimedium plants of the genus Epimedium. Examples of species within the Epimedium genus that may be used for preparing preparations having estrogenic activity include, but are not limited to *E. sagittatum, E. koreanum, E. brevicornum, E. pubescens, E. glandiflorum, E. wushanense, E. leptorrhizum, E. hunanense, E. acuminatum, E. davidii, E. fargesii, E. baicaliquizhounense, E. sutchuenense, E. caotum, E. glandolospilosum, E. zushanense, E. reticulatum, E. baojingenensis, E. simplicioflium, E. clongatum, E. ecalcaratum, E. truncatum, E. haiyangense* and *E. platypetalum*. Epimedium plants may be obtained from herbariums, planters, wholesalers in China or their business associates overseas; mention is made of commercial retailer Eu Yan Sang, Singapore.

Preferred species of Epimedium include *Epimedium brevicornum* Maxis, *Epimedium sagittatum* (Sieb. Et Zucc.) Maxim, *Epimedium pubescens* Maxim, *Epimedium wushanense* T. S. Ying, and *Epimedium koreanum* Nakai (Fain. Berberidaceae).

Estrogenic preparations and isolated estrogenic compounds may be prepared from an Epimedium plant using any part thereof, including the whole plant, or various parts of the plant, including without limitation: plant cells, tissues, seeds, embryos, leaves, stems, roots, flowers, etc. Thus, the method of this invention is not limited to the particular part of the Epimedium plant used to prepare the estrogenic preparation or isolated estrogenic compound.

Estrogenic Compositions: Pharmaceutical Compositions, Nutritional Supplements, Food Products, and Beverages:

Estrogenic compositions (including pharmaceutical compositions, nutritional supplements, food products (i.e. supplemented or fortified food), or beverages) can be prepared that comprise as an active ingredient one or more of the following: a preparation having estrogenic activity obtained from an Epimedium plant, especially a Compound III-containing preparation as described above; isolated Compound I or an estrogenic extract of an Epimedium plant enriched for Compound I; or isolated Compound III or an estrogenic preparation of an Epimedium plant enriched for Compound III.

The compositions comprise, for example, approximately from 0.1% to 100%, preferably from approximately 1% to approximately 60%, of the active ingredient.

Pharmaceutical compositions are compositions for enteral (e.g. oral) administration, and also rectal or parenteral administration, also for topical administration to warm-blooded animals (particularly humans), the pharmacological active ingredient being present alone or together with customary pharmaceutical excipients, diluents or carriers.

Pharmaceutical compositions for enteral or parenteral administration are, for example, in unit dose forms, such as dragees, tablets, capsules or suppositories, and also ampoules. They are prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture and processing the mixture of granules, if desired or necessary after the addition of suitable excipients, into tablets or dragee cores.

Suitable carriers include, especially, fillers, such as sugars, for example lactose, saccharose, mannitol or sorbitol, cellulose preparations and/or calcium phosphates, for example tricalcium phosphate or calcium hydrogen phosphate, also binders, such as starch pastes, using, for example, corn, wheat, rice or potato starch, gelatin, gum tragacanth, methyl-cellulose and/or polyvinylpyrrolidone, and, if desired, disintegrators, such as the above-mentioned starches, also carboxymethyl starch, cross-linked polyvinylpyrrolidone, agar or alginic acid or a salt thereof, such as sodium alginate.

Excipients include, especially, flow conditioners and lubricants, for example silicic acid, talc, stearic acid or salts thereof, such as magnesium or calcium stearate, and/or polyethylene glycol. Dragee cores are provided with suitable coatings that may be resistant to gastric juices, there being used, inter alia, concentrated sugar solutions which may contain gum arabic, talc, polyvinylpyrrolidone, polyethylene glycol and/or titanium dioxide, coating solutions in suitable organic solvents or solvent mixtures, or, for the preparation of enteric coatings, solutions of suitable cellulose preparations, such as acetylcellulose phthalate or hydroxypropylmethylcellulose phthalate. Colourings or pigments may be added to the tablets or dragee coatings, for example for identification purposes or to indicate different doses of active ingredient.

Further orally administrable pharmaceutical compositions include dry-filled capsules consisting of gelatin, and also soft sealed capsules consisting of gelatin and a plasticizer, such as glycerol or sorbitol. The dry-filled capsules may contain the active ingredient in the form of granules, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

Rectally administrable pharmaceutical compositions, for example, suppositories that comprise a combination of the active ingredient and a suppository base are also provided. Suitable as suppository bases are, for example, natural or synthetic triglycerides, paraffin hydrocarbons, polyethylene glycols and higher alkanols. It is also possible to use gelatin rectal capsules that comprise a combination of the active ingredient and a base material. Suitable base materials are, for example, liquid triglycerides, polyethylene glycols and paraffin hydrocarbons.

Aqueous solutions of an active ingredient in water-soluble form, for example a water-soluble salt, are particularly suitable for parenteral administration. Also suitable for parenteral administration are suspensions of the active ingredient, such as corresponding oily injection suspensions, these being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran and optionally also stabilisers.

The pharmaceutical compositions may be solid or a liquid preparation (such as a beverage, a sterile injectable solution, a powder, drops, a suspension, a syrup, a lotion, an ointment, a cream, a gel, or the like).

As in the case of the pharmaceutical compositions, the nutritional supplements, food products and beverages comprise, for example, approximately 0.1% to 100%, preferably from approximately 1% to 60%, of the active ingredient.

In one embodiment, the compounds, compositions and preparations of the invention comprise Compound I, Compound III or a mixture thereof in the absence of any other active ingredient, especially an estrogenic agent, e.g. from Epimedium.

The dose of the active ingredient may depend on various factors, such as the method of administration, species of animal, age and/or individual condition. The preferred route of administration is oral administration. The active ingredient may be administered in a range of about 0.3 μg/kg to about 20 mg/kg body weight per dose, more preferably about 0.3 mg to about 3 mg/kg body weight per dose. Therefore, for a human subject with an average body weight of 60 kg, the active ingredient may be administered in a daily dose of between 18 μg and 1.2 g, and preferred amounts to be administered to the human fall within 20 to 200 mg on a daily basis. Greater dosages can be administered for therapeutic reasons. Pharmaceutical compositions, nutritional supplements, food products and beverages of the present invention may be adapted for delivery of a daily dose of active ingredient of between about 18 μg and about 1.2 g, more typically between about 20 mg to about 200 mg.

Modulating an Estrogen Receptor and Conditions Mediated by Estrogen Receptors

The estrogenic preparations and estrogenic compounds as described herein modulate (i.e. activate) estrogen receptors. Therefore, these preparations and compounds are useful for modulating an estrogen receptor and may be used to treat a condition mediated by an estrogen receptor, such conditions including but not being limited to: premature ovarian failure, menopause, osteoporosis, menstrual irregularities, hot flushes, genital tract atrophy, lack of libido, depression, abnormalities of lipid metabolism, cardiovascular diseases, cerebrovascular diseases, atherosclerosis, coronary artery disease, strokes, and cancer. In particular, estrogenic preparations and isolated estrogenic compounds from a plant, such as an Epimedium plant, isolated therefrom may be useful for treatment of menopausal and post-menopausal women.

Given the differences in tissue distribution and the fact that ER-beta and ER-alpha may have opposing actions when expressed in the same tissue, it is desirable to have compounds that express a preference, or selectivity, for one of the ER subtypes.

Differences in tissue distribution of ER-alpha and ER-beta may be important from a pharmacological point of view, for example with respect to hormone replacement therapy in post-menopausal women, which is a matter of public health that is of great concern, and treatment of prostatic hyperplasia and carcinoma in men. Estrogen replacement therapy in postmenopausal women is associated with increased risk of breast and uterine cancers. Development of ER-beta-selective agonists, i.e. agonists that bind ER-beta with higher affinity than ER-alpha, may be useful for regulating function of the central nervous system, the cardiovascular system, the urogenital tract and bone, while reducing or avoiding side-effects associated with ER-alpha activation. In particular, a compound such as Compound III that binds with higher affinity to ER-beta over ER-alpha may provide a useful alternative to conventional estrogen replacement therapy in post-menopausal women, especially in those women who have an increased risk of endometrial cancer and/or breast cancer. In men, ER-beta-selective agonists may be useful for the treatment of prostatic hyperplasia and carcinoma while avoiding or reducing side-effects associated with ER-alpha activation.

Compound I activates both the estrogen receptor (ER)-alpha and ER-beta. Isolated Compound I, or an preparation of a plant, such as an Epimedium plant, enriched for Compound I, can be used to treat a condition mediated by an estrogen receptor, such as: premature ovarian failure, menopause, osteoporosis, menstrual irregularities, hot flushes, genital tract atrophy, lack of libido, depression, abnormalities of lipid metabolism, cardiovascular diseases, cerebrovascular diseases, atherosclerosis, coronary artery disease, strokes, and cancer.

Compound II has no detectable estrogenic activity under the conditions described herein. Compound II is useful as a marker to identify fraction(s) of an Epimedium plant that contain Compound III, since Compound II is present in relatively large amounts in extracts of Epimedium plant, co-elutes with Compound III and is easily detected by MS and NMR. Compound II may have pharmacological activities observed in related prenylflavones, such as anti-platelet activity (Chen et al., 1996). Compound III activates ER-beta more strongly than it activates ER-alpha. Compound III, or preparations of an Epimedium plant enriched for Compound III, may be useful for treating conditions that are mediated by an estrogen receptor, and in particular, Compound III may be useful for treating a condition mediated by ER-beta while reducing or minimizing side-effects associated with activation of ER-alpha. Because Compound III activates ER-beta more strongly than ER-alpha, Compound III may be useful for regulating functions in tissues that express ER-beta as their predominant ER isoform, such as tissues of the central nervous system, the cardiovascular system, and the gastrointestinal and urogenital tracts, while reducing the incidence of side-effects resulting from stimulation of ER-alpha (such as breast cancer and endometrial cancer). Compound III can be further used to regulate anti-proliferative and anti-oxidant functions which are mediated at least in part through ER-beta. Thus Compound III may be used to treat hormone-dependent cancers like breast and endometrial cancers in women and prostate cancer in men, and other conditions associated with oxidative damage such as Alzheimer's disease.

(i) Menopause

During the period of menopause and postmenopause, women often experience one or more symptoms due to declining estrogen levels, such as hot flushes, osteoporosis, depression, mood swings, sleeping disorders, atrophy of the breast and reproductive tissues, vaginal dryness and joint pain. An effective way of relieving menopausal symptoms involves estrogen replacement therapy. However, traditional hormone replacement therapy, using currently available forms of estrogens, brings about undesirable side effects, such as weight gain and breast tenderness. In addition, long-term estrogen therapy is also associated with a slight but significant increase in the risk of developing breast carcinoma and endometrial carcinoma. Epidemiological data show that a diet rich in phytoestrogen such as genistein found in soy, correlates with a reduction in the number of hot flushes (Tham, et al., 1998) and a lower incidence of breast cancer in Oriental women (Lee, et al., 1991). There is some evidence to suggest that phytoestrogens may have different pharmacological actions as compared to endogenous estradiol, and that phytoestrogens may selectively modulate the actions of estrogen receptors in cells (Diel, et al., 2001).

The differences in tissue distribution of ER-alpha and ER-beta may be important with respect to hormone replacement therapy in post-menopausal women, which is a great public health concern, and treatment of prostatic hyperplasia and carcinoma in men. Estrogen replacement therapy in postmenopausal women is associated with increased risk of breast and uterine cancers that may be mediated by ER-alpha. Development of alternative ER-agonists, in particular ER-beta-selective agonists (i.e. agonists that bind ER-beta with higher affinity than ER-alpha), may be useful for regulating function of the central nervous system, the cardiovascular system, the urogenital tract and bone, while reducing or avoiding side-effects, such as side-effects associated with ER-alpha activation. In particular, a compound that binds with higher affinity to ER-beta over ER-alpha may provide a useful alternative to conventional estrogen replacement therapy in post-menopausal women who have an increased risk of endometrial and breast cancers.

(ii) Breast and Mammary Cancer

Studies in the human and rodent breasts indicate that ER-beta is much more abundantly expressed than ER-alpha in these tissues. Studies in the breast of BERKO (ER-beta −/− knockout) mice revealed abnormal epithelial growth and severe cystic breast disease as the mice age (Gustafsson, et al., 2000). In the human, ER-beta is expressed at high levels in stromal breast tissues but is significantly reduced in pre-invasive mammary tumors. This marked an early decrease in levels of ER-beta protein was associated with other criteria of cell proliferation in high grade ductal carcinoma-in-situ and suggest a protective effect of ER-beta against the mitogenic activity of estrogens in mammary premalignant tissue (Roger, et al., 2001). Ligands specific to ER-beta may therefore be of use for the prophylaxis or chemoprevention and treatment of breast carcinoma.

(iii) Cardiovascular System

Both ER-alpha and ER-beta are expressed in vascular tissue. However, in vascular tissue, experimental denudation of the endothelial layer leading to smooth muscle proliferation is accompanied by a huge increase (up to 80-fold) of ER-beta in smooth muscle cells, whereas expression of ER-alpha is unaffected. This result suggests that the protective effect of estrogens on vascular tissue inferred from epidemiological studies involves inhibition of smooth muscle proliferation mediated through ER-beta (Lindner, et al., 1998). Thus, drugs that regulate ER-beta action may be useful for treating diseases where vascular proliferation is important, such as strokes and coronary arterial disease.

(iv) Central Nervous System

In the central nervous system, estrogens are associated with a plethora of regulatory activities. For example, ER signaling regulates reproduction and sexual behavior.

In the human brain, the highest expression of ER-alpha has been found in restricted areas of the amygdala and hypothalamus. In contrast, ER-beta expression is low in these areas. ER-beta is most abundantly expressed in hippocampus, claustrum and cerebral cortex suggesting a role of ER-beta in the modulation of cognition, memory and motor function in the human (Osterlund, et al., 2000). The brains of BERKO mice, show several morphological abnormalities. There is a regional neuronal hypocellularity in the brain, with severe neuronal deficit in the somatosensory cortex, especially layers II, III, IV and V, and a remarkable proliferation of astroglial cells in the limbic system but not in the cortex. As BERKO mice age, the neuronal deficit becomes more pronounced and by 2 years there is degeneration of neuronal cell bodies throughout the brain, especially in the substantia nigra (Wang, et al., 2001). ER-beta is believed to play a role in neuronal survival, and consequently, compounds that activate ER-beta may be useful for the prevention and treatment of degenerative diseases of the central nervous system, such as Alzheimer's disease and Parkinson's disease, as well as disorders resulting from trauma and stroke in the brain. Thus administration of activators of ERs may affect important parameters of neural function, including cognition and memory.

(v) Urogenital Tract

Another tissue that expresses ER-beta is the urogenital tract. Both transitional epithelium in the bladder, and the epithelium of the urethra, the seminal vesicles, the prostate and kidney pelvis express significant quantities of ER-beta mRNA. The expression of ER-alpha in these tissues is less pronounced and the effect on urinary incontinence of estrogens might be mediated through ER-beta.

(vi) The Prostate Gland

Prostatic epithelial cells express ER-beta in normal rats and mice. In prostates from BERKO mice, androgen receptor levels are elevated and the tissue is hyperplastic, suggesting an important role of ER-beta in the male for regulating the growth of prostate tissue (Weihua, et al., 2001). Studies in human prostate cancer indicate that loss of ER-beta expression is associated with progression from normal prostate epithelium to prostate cancer (Horvath, et al., 2001). These data suggest that ligands that activate ER-beta may be useful in the prevention and/or clinical management of prostatic hyperplasia and prostate cancer. ER-beta-selective agonists may be useful for the treatment of prostatic hyperplasia and carcinoma while avoiding or reducing side-effects associated with ER-alpha activation, such as deep vein thrombosis, and strokes due to excessive blood clotting.

(vii) Reproduction

BERKO female mice have reduced fertility (Pettersson, et al., 2001). Poor reproductive capacity in BERKO mice is due to defects in both the ovary and uterus. Unlike ERKO (ER-alpha −/− knockout) mice, where ovarian defects are the result of pituitary dysfunction, the defects of BERKO mice are in the ovary itself. There is a marked paucity of corpora lutea and an increase in the number of follicles with premature atresia. Uterine dysfunction also contributes to infertility in BERKO mice. ER-beta, but not hER-alpha, is expressed in the human testis. Some patients with azoospermia do not express ER-beta in the testis, suggesting that ER-beta agonists may be useful for treating certain kinds of male infertility. Thus discovery of ligands that can activate ER-beta specifically may be of use in treating both male and female infertility.

(viii) Cardiovascular Disease and Lipoprotein Metabolism

Epidemiological, clinical trial data, and basic science studies suggest a causal inverse relationship between phytoestrogens and cardiovascular disease. Populations with high intakes of dietary phytoestrogens have lower rates of cardiovascular disease (Tham, et al., 1998). Many epidemiological studies indicate that hormone replacement therapy is associated with reduction of the risks of coronary heart disease and has a possible cardioprotective role. Several human trials have reported cholesterol-lowering effects with phytoestrogens. Thus a significant reduction in total cholesterol was noted in premenopausal women when they consumed soy products with 45 mg conjugated isoflavones/day relative to levels during a control period when they were fed isoflavone-free soy products. In another study, hypercholesterolemic post-menopausal women were randomly assigned to 6 months of 40 g protein supplementation/day of casein or soy protein. Soy products lowered non high-density lipoprotein (non-HDL) cholesterol and increased HDL cholesterol significantly. Both soy groups experienced improved total cholesterol/low-density lipoprotein/cholesterol ratios.

(ix) Cancer

Both endogenous and exogenous sex-hormones have been associated with various cancers. High levels of biologically active androgen or estrogens are associated with increased risk of prostate cancer in men and with increased risk of ovarian and breast cancer in women. Despite the positive association of endogenous and exogenous estrogens with cancers, plant estrogens are inversely associated with cancer. It is well established that cancer risks differ strikingly in various populations of the world. Hormone-related cancers of the breast, ovary, endometrium and prostate have been reported to vary by as much as 5- to 20-fold between populations. The lowest rates were typically observed in Asian populations, which populations have plant-based diets with a high content of phytoestrogens. In a case-control study (Ingram D, Sanders K, Kolybaba M, Lopez D. Case-control study of phyto-oestrogens and breast cancer. Lancet. Oct. 4, 1997;350(9083):990–4), it was reported that a significant reduction in breast cancer risk among pre- and post menopausal women who consumed phytoestrogens. In a study of Asian-Americans, it was reported that tofu consumption was significantly and inversely associated with breast cancer (Tham 1998). A case-control study in Singapore showed that soy products were inversely and animal product positively associated with breast cancer in premenopausal women (Lee, et al., 1991). Soy and fiber consumption was also associated with a reduced risk of endometrial cancer. Thus discovery of new phyto-agonists which activate ERs, in particular ER-beta, may provide a valuable alternative treating many conditions in men and women. This is in relation to many important diseases that affect the cardiovascular health and cancer risk of aging populations.

The invention is further illustrated by the following non-limiting examples.

EXAMPLE 1

Screening of Herbs for Estrogenic Activity

Eleven Traditional Chinese herbs with reported 'Yin' or 'Yang' action in traditional texts were purchased from a commercial retailer (obtained from Eu Yan Sang, Singapore) and screened for estrogen receptor activity using a cell-based reporter gene assay. These herbs are identified in Table 1. Herbs were ground, mixed with appropriate solvents and allowed to soak for 5–7 days at 37° C. in 100% ethanol, after which the extract in the supernatant was filtered with Whatman Grade I (11 μm pore size) filter paper. The herbal residue was re-extracted a second time with the same solvent for 2–3 hours. Filtered extracts were combined and dried in a rotary evaporator. Dried extracts were weighed and resuspended in 100% ethanol or methanol to a concentration of 50 mg/ml. Each herbal extract was screened for estrogenic activity in-vitro at a final concentration of 50 μg/ml.

To assay estrogen receptor agonist activity, Hela cells were grown in 24-well microtiter plates and then transiently co-transfected with two plasmids using lipofectamine. The first plasmid comprised DNA encoding human estrogen receptor (either ER-alpha or ER-beta), and the second plasmid comprised an estrogen-driven reporter system comprising: a luciferase reporter gene (LUC) whose transcription is under the control of upstream regulatory elements comprising 4 copies of the vitelogenin estrogen response element (ERE) cloned into the mouse mammary tumor virus (MMTV) promoter (the full name for the reporter system being "MMTV-ERE-LUC"). Cells were exposed to herbal extracts in RPMI 1640 medium, supplemented with 10% charcoal-treated fetal calf serum, 2 mM L-glutamine, 0.1 mM non-essential amino acids and 1 mM sodium pyruvate for 42–48 hours at 37° C. in a 5% carbon dioxide incubator. Concurrently, cells exposed to estradiol (1 nM) served as positive controls. Replicate wells exposed to the solvent in which herbal extracts were dissolved (i.e. ethanol or methanol) were used as negative controls. After the 42–48 hr incubation period, cells were rinsed with phosphate buffered saline(PBS), lysis buffer (Promega Corp) was added, and cell lysates collected for measurement of luciferase activity with a luminometer. Estrogenic activity of the herbal extracts is expressed as fold-increase in luciferase activity as compared to that observed in negative control cells. All data points are in triplicate.

From the preliminary screening of the eleven herbal extracts, Epimedium herb (mixture of *E. Brevicorum*) extracted with 100% ethanol was found to exhibit the highest ER-alpha stimulatory activity, increasing luciferase activity 13.7 fold above controls exposed to vehicle alone (Table 1). This activity was about 54.7% of that observed for estradiol (1 nM).

TABLE 1

Screening of herbs for estrogenic activity using ER-alpha and MMTV-ERE-LUC reporter gene in Hela cells.

| Herbal extract | Estrogenic activity (fold increase over vehicle) | Activity compared to estradiol (1 nM) (%) |
|---|---|---|
| Epimedium species | 13.7 | 54.7 |
| Dioscorea opposita | 2.8 | 8 |
| Anemarrhena asphodeloides | 4.2 | 18 |
| Curculigo orchioides | 0.9 | 2.9 |
| Cuscuta chinensis | 1.6 | 7.6 |
| Polygonatum kingianum | 0.8 | 2.7 |
| Morinda officinalis | 1.0 | 3.9 |
| Psoralea corylifoloa | 5.9 | 23.1 |
| Angelica sinensis | 0.7 | 2.6 |
| Lycium chinense | 1.3 | 5 |
| Radix astragali | 1.1 | 4.2 |

EXAMPLE 2

Method for Extracting Estrogenic Compound(s) from Epimedium Herb

Epimedium herb extract (ES crude extract) was prepared as described in Example 1, except to vary the solvent. Water and various combinations of ethanol and methanol in water were tested as solvents. Extracts prepared using 100% water as solvent was prepared by boiling Epimedium herb with water for 2 hours. Extracts prepared with 100% alcohol or a mixture of alcohol and water as solvent were prepared by soaking the Epimedium herb in solvent for 5–7 days at 37° C., to obtain ES crude extract.

The ES crude extracts thus obtained were tested for estrogenic activity as described in Example I (see Table 2). As shown in Table 2, under the present conditions, 100% ethanol was found to be the most effective of the solvents tested for extracting estrogenic activity from an Epimedium plant. The traditional method of boiling with 100% water resulted in the medium estrogenic activity.

For all subsequent experiments, an Epimedium herb was extracted with 100% ethanol to obtain ES crude extract.

TABLE 2

Estrogenic activity of ES crude extracts obtained by extraction with various solvents; extracts were tested at a concentration of 50 μg/ml.

| Solvent used to prepare extract | Estrogenic activity (% of 1 nM estradiol) on ER-alpha | Estrogenic activity (% of 1 nM estradiol) on ER-beta |
|---|---|---|
| 100% water* | 30.09 | 15.23 |
| 10% ethanol: 90% water | 13.36 | 3.48 |
| 20% ethanol: 80% water | 23.76 | 21.65 |
| 30% ethanol: 70% water | 22.60 | 50.46 |
| 70% ethanol: 30% water | 38.9 | N.D.# |

TABLE 2-continued

Estrogenic activity of ES crude extracts obtained by extraction with various solvents; extracts were tested at a concentration of 50 μg/ml.

| Solvent used to prepare extract | Estrogenic activity (% of 1 nM estradiol) on ER-alpha | Estrogenic activity (% of 1 nM estradiol) on ER-beta |
|---|---|---|
| 100% ethanol | 80.7 | 171.5 |
| 70% methanol: 30% water | 63.8 | N.D. |
| 100% methanol | 46.5 | N.D. |

*Boiled for 2 hours at 100° C.
N.D.: Not done

EXAMPLE 3

Dose-response Comparisons of ES Crude Extract with Known Estrogen Receptor Ligands Epimedium herb extract (ES crude extract) was prepared with 100% ethanol as described Example 2. Table 3 shows the dose-response relationship of test compound or extract assayed for estrogenic activity as described in Example 1, wherein the estrogen receptor was ER-alpha, and wherein test compounds include: (1) ES crude extract; (2) the physiological estrogen, estradiol (E2); (3) the phytoestrogen, genistein; and (4) the estrogen antagonist, tamoxifen. Increasing concentrations of test compounds or ES crude extract were assayed.

Estrogenic activity of the test compounds and ES crude extract are shown in Table 3, expressed as fold increase in luciferase activity compared to cells exposed to vehicle (ethanol) only. Each data point is the mean±SE of triplicate samples. Both estradiol and genistein displayed strong estrogenic activity with maximal stimulation of ER-alpha by genistein observed at a dose of 500 ng/ml. The dose-response of ES crude extract, at doses ranging from 0.5 ng/ml to 50 μg/ml, showed detectable activity at 50 ng/ml, rising to a maximum at the dose of 50 μg/ml. ES crude extract activity was about 50% of estradiol (500 ng) at the highest dose. The $EC_{50}$ of genistein was about 110 ng/ml. Tamoxifen (an estrogen antagonist) did not activate ER-alpha under these conditions.

TABLE 3

Dose response of ES crude extract compared to estradiol, genistein and tamoxifen on ER-alpha reporter gene assay.

| Dose | Estradiol Estrogenic activity | Genistein Estrogenic activity | Tamoxifen Estrogenic activity | ES crude extract Estrogenic activity |
|---|---|---|---|---|
| 0.5 ng/ml | 17.528 ± 1.193 | 1.505 ± 0.077 | 1.526 ± 0.084 | 0.879 ± 0.027 |
| 5 ng/ml | 19.015 ± 0.219 | 2.981 ± 0.168 | 0.799 ± 0.055 | 1.037 ± 0.075 |
| 50 ng/ml | 21.133 ± 1.528 | 6.690 ± 0.752 | 0.493 ± 0.045 | 2.004 ± 0.127 |
| 500 ng/ml | 26.696 ± 0.723 | 31.205 ± 1.336 | 0.524 ± 0.062 | 5.029 ± 0.146 |
| 5 μg/ml | 23.175 ± 0.775 | 31.686 ± 1.795 | 0.731 ± 0.031 | 9.162 ± 0.538 |
| 50 μg/ml | N.D.# | N.D. | 0.009 ± 0.009 | 13.689 ± 0.330 |
| 100 μg/ml | N.D. | N.D. | N.D. | 14.484 ± 0.609 |

: Not done

EXAMPLE 4

ES Crude Extract Activity on ER-Alpha can be Blocked by Tamoxifen

Crystallographic data indicate that ER antagonists act by binding to the ER-alpha ligand-binding pocket (LBD) (Brzozowski 1997, Pike, 1999). To determine whether ES crude extract contained compounds that bind to the ligand-binding pocket of ER-alpha LBD, we tested whether tamoxifen (an estrogen receptor antagonist) could block the estrogenic activity of ES crude extract (prepared with 100% ethanol as described in Example 2). Hela cells transfected with ER-alpha and luciferase reporter gene, as described in Example 1, were exposed to increasing doses of tamoxifen (an estrogen antagonist) in the presence of fixed dose of ES crude extract (50 μg/ml) (prepared with 100% ethanol as described Example 2) or estradiol (1 nM). Activity of both estradiol and ES crude extract can be completely blocked by 500 ng/ml of tamoxifen, suggesting that ES crude extract contains one or more compounds that bind to ER-LBD.

EXAMPLE 5

Assay of Antagonistic or Synergistic Action of ES Crude Extract on Estradiol Activity Epimedium herb extract (ES crude extract) was prepared with 100% ethanol as described Example 2. Estrogenic activity was assayed as described in Example 1. Cells were exposed to indicated doses of ES crude extract or genistein, in the presence of fixed doses estradiol (1 nM). The estrogenic activity of ES crude extract (at doses ranging from 0.5 ng/ml to 50 μg/ml) and estradiol (1 nM) together was no different than that observed with estradiol alone. Thus ES crude extract, at doses ranging from 0.5 ng/ml to 50 μg/ml, did not inhibit or augment the activity of estradiol alone. In the same way, genistein (at doses ranging from 0.5 ng/ml to 50 μg/ml) also did not display any antagonistic or synergistic effects on estradiol activity.

EXAMPLE 6

ES Crude Extract Agonistic Activity is Specific to ER

ES crude extract was prepared with 100% ethanol as described Example 2. Plasmids encoding either PR (progesterone receptor), GR (glucocorticoid receptor) and AR (androgen receptor) were co-expressed with a reporter gene, (PRE)2-Luc, that contains hormone-response elements that are common to all three receptors; PR, GR, and AR activity was determined by comparing luciferase activity in test cells as compared with control cells exposed to vehicle only, analogous to determination of estrogenic activity in Example 1. Estrogenic activity was measured using ER-alpha and the MMTV-ERE-LUC reporter gene as described in Example 1.

The presence of ES crude extract in doses from 50 ng/ml to 100 µg/ml did not have any effect on related steroid receptors, PR, GR or AR reporter gene systems. In contrast, ES crude extract displayed strong estrogenic activity, resulting in a maximal 14-fold increase in ER-alpha activity at a dose of 50 µg/ml with $EC_{50}$ of about 150 ng/ml, comparable to that observed for genistein (110 ng/ml) in Example 3. Thus, estrogen receptor agonistic activity of ES crude extract was specific to ER and no cross-reaction was observed with related members of the steroid receptor superfamily under the conditions tested. ES crude extract (at 100 ug/mL) was also comparable in activity to genistein (at 500 ng/mL), one of the most potent phytoestrogens.

EXAMPLE 7

Assay for Antagonistic or Synergistic Effects on GR, PR and AR

ES crude extract was prepared with 100% ethanol as solvent, as described Example 2. Addition of ES crude extract at doses from 5 ng/ml to 100 µg/ml did not exert any significant inhibitory or synergistic effect on GR, PR and AR reporter gene systems, in the presence of fixed doses of: (1) hydrocortisone, 1 nM; (2) progesterone, 100 nM; or (3) dihydrotestosterone, 1 nM respectively.

EXAMPLE 8

Methods for Fractionation of ES Crude Extract Using Diol and C18 Solid Phase Columns Bioassay-guided fractionation was performed to identify the bioactive compound(s). Estrogenic activity was assayed as described in Example 1. ES crude extract was prepared with 100% ethanol as solvent, as described Example 2, from ground dried aerial parts of Epimedium herb (200 gm) and absolute ethanol (800 ml). The ES crude extract thus obtained was concentrated in vacuo, and subjected to polyamide column, and eluted with methanol (MeOH). ES extract collected from polyamide column was then subjected to Diol flash vacuum chromatography using solvents of increasing gradient profile: hexane, 1:1 hexane:$CH_2Cl_2$ (dichloromethane); $CH_2Cl_2$, 3:7 EtOAc (ethyl acetate): $CH_2Cl_2$, 3:2 EtOAc:$CH_2Cl_2$, EtOAc, 4:1 EtOAc:MeOH, and a final wash with MeOH. Eluted fractions (D1 to D8) were evaporated to dryness, weighed, and resuspended in ethanol at three dilutions for measurement of ER-alpha activity as described in Example 1.

Measurement for estrogenic activity indicated that the most potent fraction was D3, eluted with 100% dichloromethane. At a dose of 25 µg/ml, estrogenic activity of D3 fraction was over 60-fold higher than vehicle compared to 10-fold observed with ES crude extract (at 25 µg/ml). Thus dichloromethane elution in Diol column has resulted in a fraction with 6-fold increase in potency, estrogenic activity being even higher than that observed with estradiol (1 nM; 0.272 ng/ml). Fractions D2, D4, D5 (eluted with 50% dichloromethane in hexane, 30% ethyl acetate in dichloromethane and 60% ethyl acetate in dichloromethane respectively) showed estrogenic activity about 2–4 fold higher than for equivalent concentrations of crude extract. In contrast, fractions D1, D6, D7, D8 displayed lower potency compared to the ES crude extract. Thus Diol solid phase extraction is an effective method for obtaining fractions that are enriched for estrogenic compounds.

Solid phase fractionation was also performed using C18 columns. ES crude extract (prepared as described in Example 2) was applied to C18 glass columns and eluted with double volumes of water, followed by different combinations of $H_2O$-MeOH mixtures of decreasing polarity resulting in collection of fractions C1 to C7. Estrogenic activity in eluates was measured as described in Example 1. Maximal ER-alpha activity was observed in the C4 (70% methanol in water) and C5 (90% methanol in water). Eluates with a weaker estrogenic activity was also detected in the C7 (100% methanol) fraction. These results suggest that estrogenic activity was likely to be due to more than one species of estrogenic compound present in the ES crude extract.

EXAMPLE 9

HPLC Fingerprinting of Diol Fraction D3

D3 (eluted with 100% dichloromethane) was the most active fraction from Diol solid phase fractionation obtained in Example 8. D3 was further fractionated and analyzed using HPLC (Luna Phenomenex C18; 5 µm 150 mm×10 mm) column. Using a gradient of 30% acetonitrile (ACN) in $H_2O$ to 100% ACN, D3 was observed to yield a chromatogram pattern of more than 50 peaks. Thirty-one HPLC fractions were collected, dried, resuspended in ethanol and tested for estrogenic activity using the estrogen activity assay described in Example 1. The final concentrations of the fractions in the assay were 5 µg/ml. Estradiol (1 nM) and ES crude extract were assayed for comparison. It was observed that the most estrogenic activity resided in fraction 16 (eluting between 12.31 and 13.00 min), and fraction 17 (eluting between 13.01 and 14.00 min). Thus, this HPLC pattern, especially peaks corresponding to active fractions 16 and 17 can be used to standardize and classify the estrogenic potency of various types of ES extracts.

EXAMPLE 10

Methods for Isolation of Compound I

Although cell-based biological testing showed that the majority of the estrogenic activity resided in D3, 100% dichloromethane fraction (obtained from Example 8), there was insufficient material for further purification. Therefore the D4 fraction from Example 8 (eluted with 3:7 EtOAc:$CH_2Cl_2$) was used for further purification of the estrogenic activity.

Fractionation of D4 on HPLC (Luna Phenomenex C18 5 µm 150 mm×10 mm) using a gradient of 20% acetonitrile (ACN) to 90% ACN in $H_2O$ over 20 minutes, followed by a flush for 6 minutes with 100% ACN, yielded 27 fractions. Estrogen receptor bioassay (performed as described in Example 1) of each of these fractions indicated that estrogenic activity again resided mainly in HPLC fractions 16 and 17, which under these conditions eluted between 15.01–16.00 min and 16.01–16.30 min respectively. These fractions were dried down, weighed and subjected to extensive 1D ($^1$H) and 2D NMR ($^1$H-$^1$H COSY, $^1$H-$^{13}$C gHSQC and $^1$H-13C gHMBC) spectroscopy and negative mass spectrometry (HRESIMS).

EXAMPLE 11

Determination of Structure and Yield of Compound I (MW: 338)

When analyzed, HPLC fraction 17 from Example 10 was found to contain the compound designated "Compound I".

Yield and purity: From 200 gm of dried plant material, 11 gm of crude extract was obtained. From this amount of crude extract, Compound I, weighing 1.5 mg (0.14% of dried crude extract), was isolated as a stable pale yellow compound of 85% purity.

Structure: Fraction 17, isolated as described above in Example 10, was dried down and examined by negative (M–H)⁻ HRESIMS. The mass spectra indicated the presence of predominantly two compounds of MW 338 (designated Compound I) and MW 438 (designated Compound II).

Compound I gave a (M–H)⁻ HRESIMS ($C_{20}H_{18}O_5$, Δmmu=2.4) consistent with 12 degrees of unsaturation. The structure of Compound I was determined by (a) 1D-NMR, (b) 2D-NMR: $^1H$-$^1H$ COSY, $^1H$-$^{13}C$ gHSQC and $^1H$-$^{13}C$ gHMBC spectra analyses.

Analyses of the $^1H$ and gHSQC NMR data showed chemical shift values for a 1,1,2 trisubstituted double bond ($^{13}C$: 134.0, 123.0 ppm, $^1H$: δ5.35 (t, J=6.3 Hz)), an alpha-, beta-unsaturated ketone ($^{13}C$: 184.0, 167.0, 103.5 ppm, $^1H$: δ6.52 (s)) and two olefinic methyl groups ($^{13}C$: 26.0, 19.8 ppm, $^1H$: δ1.77 (s), 1.75 (s)). Also present were 12 $SP^2$ $^{13}C$ resonances, consistent with a 1,2,3,5 tetrasubstituted aromatic system ($^{13}C$: 160.5, 130.0, 129.0, 127.0, 123.0, 115.0 ppm, $^1H$: δ7.66 (d, J=8.8 Hz), 7.66 (d, J=2.2 Hz) 6.88 (dd, J=8.8, 2.0 Hz)), and a 1,2,4 trisubstituted aromatic system ($^{13}C$: 167.0, 163.0, 159.5, 105.0, 100.0, 95.0 ppm, $^1H$: δ6.41 (d, J=1.8 Hz), 6.18 (d, J=1.8 Hz)). This left one degree of unsaturation implying that the molecule was tricyclic. Further analysis of the COSY and gHMBC spectra showed that the NMR data was entirely consistent with the known prenylflavone (yinyanghuo D) (Chen et al., 1996).

Chemical Structure of Compound I (Formula I)

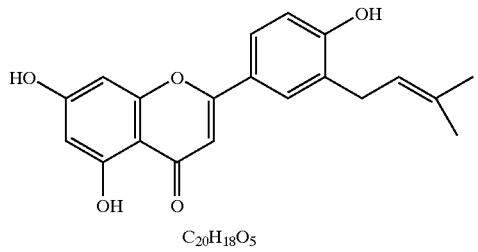

$C_{20}H_{18}O_5$

EXAMPLE 12

Methods to Isolate Compound II

Preliminary negative (M–H)⁻ HRESIMS MS analysis of HPLC fractions 16 and 17 of both D3(Example 10) and D4 (Example 11) indicated the presence of another compound of MW 438. Since this compound was present in minute quantities, fractions 16 and 17 of several HPLC runs (starting with both D3 and D4 fractions) were combined and re-subjected to a second HPLC (Luna Phenomenex C18 5 μm 150 mm×10 mm) using an isocratic mobile phase of 43% ACN in $H_2O$ over 20 minutes. Six fractions designated AF1 to AF6 were obtained (FIG. 15) from the HPLC run and the fractions were tested for activity on ER-alpha and ER-beta reporter gene expression systems.

AF1 (elution time: 8.01–9.45 min) and AF2 (elution time: 10.01–11.00 min) of this second HPLC run activated ER-beta strongly but had only very weak ER alpha activity in repeated experiments, suggesting that these fractions contained an ER-beta estrogen receptor-selective agonist. In contrast, fraction AF6 (elution time: 15.01–16.15 min) was able to activate both ER-alpha and ER-beta equally. Mass spectrometric analyses of fractions AF1 and AF2 showed the presence of Compound II and Compound III of MW 438. Compound I (MW 338) was not detected in the fractions AF1 and AF2, but was present in AF6, (as determined by mass spectrometric analysis. On the other hand, Compound II and III (both of MW 438) were not detected in fraction AF6. Fraction AF1, was dried down, weighed and subjected to extensive 1D & 2D NMR spectroscopy ($^1H$, COSY, gHSQC, gHMBC), and negative mass spectrometry (HRESIMS).

EXAMPLE 13

Structure Elucidation of Compound II (MW:438)

Compound II gave a molecular ion in the Electron spray isolation mass spectrometry (–)–ESIMS [(M–H)⁻ m/z 437.1631 Δmmu 3.1] consistent with the molecular formula $C_{25}H_{26}O_7$, corresponding to thirteen double bond equivalents. Analysis of the NMR data for Compound II readily identified the structure as an isoflavone similar in structure to that for yinyanghuo D, but differing in substitution of the pendant aryl system. From the NMR data it became apparent that this aryl group was symmetrical [$^{13}C$: 160.5, 129.5, 129.5, 128.0, 128.0, 121.0 ppm; $^1H$: δ7.59 (s), 7.59 (s)]. Obvious were resonances consistent with two 1,1-disubstituted double bonds [$^{13}C$: 148.0, 112.0 ppm; $^1H$: δ4.92 (d, J=2.5 Hz), 4.80 (d, J=2.5 Hz)], two hydroxy methines [$^{13}C$: 77.5 ppm; $^1H$: δ4.37 (ddd, J=4.0, 4.0, 3.4 Hz)], two olefinic methyls [$^{13}C$: 18.1 ppm; $^1H$: δ1.80 (s)] and two benzylic methylenes [$^{13}C$: 39.0 ppm; $^1H$: δ2.94 (m)] Important gHMBC correlations from δ6.52 to 121.0 ppm, δ7.59 to 39.0 ppm, and from δ2.94 to 160.5, 129.5 and 128.0 ppm allowed for the gross structure to be elucidated as shown.

Chemical Structure of Compound II (Formula II)

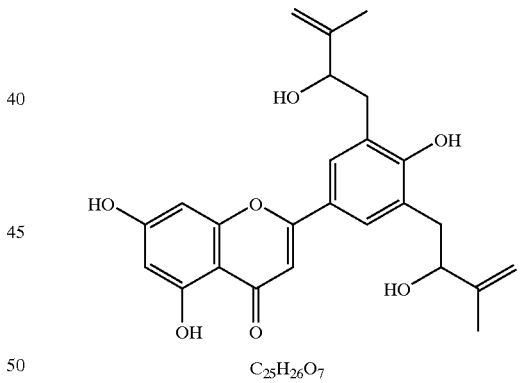

$C_{25}H_{26}O_7$

EXAMPLE 14

Methods to Isolate Compound III

Fractions AF1 and AF2 from Example 12 were further separated by HPLC using RP Amide column and the mobile phase used was gradient from 50% acetonitrile (ACN) in $H_2O$ to 60% ACN in $H_2O$ over 10 minutes, and stayed isocratic for another 10 minutes. Compound III was collected at retention time of 8.00–8.45 minute, separated from Compound II which eluted at 9.00–9.50 minute.

EXAMPLE 15

Structure of Compound III (MW: 438)

Compound III, obtained as a yellow powder, gave a molecular ion in the (–)–ESIMS [(M–H)⁻ m/z 437.1579

Δmmu 2.1] consistent with the molecular formula $C_{25}H_{26}O_7$, which was same with that of Compound II. Analysis of the NMR data for Compound II and III indicated that the two compounds only differ from each other at the substitution of the pendant aryl system. From the NMR data it apparently showed a symmetrical [3,4,5-trisubstituted aromatic system ($^{13}$C:163.0, 131.5, 129.3, 125.9, 124.9, 122.8 ppm; $^1$H: δ7.84 (s), 7.67 (s)]. Calculation of the molecular unsaturation showed that in addition to the known three aromatic rings, there was another cyclic system in the molecule. The proton signals at [$^1$H: δ5.39 (d, J=5.0 Hz), δ4.36 (d, J=5.0 Hz)] had a cross peak with the carbon signal at δ163.0 respectively in the gHMBC spectrum, and they also coupled to each other in the $^1$H-$^1$H COSY spectrum. Comparing the NMR data of Compound III with that of Compound II, the signal double bands disappeared, instead of which there were ($^{13}$C: 25.8, 25.3 ppm) belonging to a terminal two methyl signals [$^1$H: δ1.30 (s), 1.23 (s)] at the high field. The above analysis is consistent with a furan cycle attached to the pendent aryl system at C-4' and C-5' position. Important gHMBC correlations from δ1.30, 1.23 to 71.8 ppm, indicate that an hydroxyl group is linked to the carbon together with the two methyl group. Combined analysis of MS, 1D and 2D NMR allowed for the gross structure to be elucidated as shown.

Chemical Structure of Compound III (Formula III)

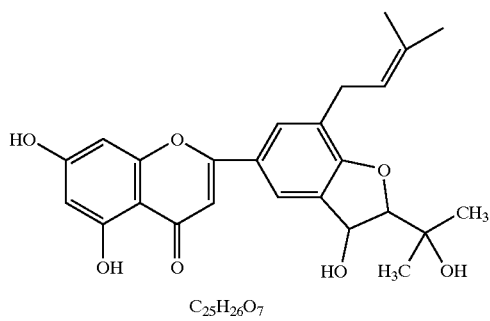

$C_{25}H_{26}O_7$

EXAMPLE 16

Action of Compound I and Compound III on ER-alpha and ER-beta Estrogen Receptors The estrogenic activity of two doses of each fraction of the second HPLC run from Example 14 was performed. AF1 (containing Compound III) displayed dose-dependent ER-beta stimulatory activity that was stronger than that observed for estradiol, but has only 26% of the ER-alpha activity of estradiol. In contrast, Fraction AF6 displayed strong ER-alpha and ER-beta activity in a manner similar to that of estradiol.

TABLE 4

Estrogenic activity (expressed as fold increased over vehicle) of Compound I (AF6) and Compound III (AF1) on ER-alpha and ER-beta estrogen receptors.

| Dose | AF6 (MW: 338) | | AF1 (MW: 438) | |
| --- | --- | --- | --- | --- |
| | ER-alpha | ER-beta | ER-alpha | ER-beta |
| 0.05 μg/ml | 4.940 ± 0.184 | 2.598 ± 0.201 | 1.031 ± 0.198 | 1.514 ± 0.266 |
| 0.5 μg/ml | 9.089 ± 0.351 | 18.763 ± 0.160 | 2.357 ± 0.178 | 6.093 ± 0.735 |
| 5 μg/ml | 11.618 ± 0.708 | 13.289 ± 1.813 | 2.694 ± 0.411 | 23.132 ± 0.872 |

Cells were transfected with either ER-alpha or ER-beta and estrogenic activity measured as described in Example 1. Fraction AF6 displays has estrogen receptor agonist activity on both ER-alpha and ER-beta estrogen receptors, in a manner similar to that of estradiol at 1 nM. On the other hand, fraction AF1 demonstrated a dose-dependent ER-beta estrogen receptor agonist activity that was stronger than that observed for ER-alpha estrogen receptors.

Based on this assay, Compound III (at 5 μg/ml) activates ER-beta more strongly than ER-alpha by a factor of about nine-fold. Compound III at 15 ng/ml has ER-beta activity equivalent to estradiol at 1 nM.

Bibliography

Brzozowski A M, Pike A C, Dauter Z, Hubbard R E, Bonn T, Engstrom O, Ohman L, Greene G L, Gustafsson J A, Carlquist M. 1997 Molecular basis of agonism and antagonism in the oestrogen receptor. Nature. 389:753–8.

Barkhem T, Carlsson B, Nilsson Y, Enmark E, Gustafsson J, Nilsson S. 1998 Differential response of estrogen receptor alpha and estrogen receptor beta to partial estrogen agonists/antagonists. Mol Pharmacol. 54:105–12.

Chen C C, Huang Y L, Sun C M, Shen C C. 1996. New prenylflavones from the leaves of Epimedium saggitatum. J Nat Prod. 59:412–4.

Conneely O M. 2001. Perspective: female steroid hormone action. Endocrinology. 142:2194–9.

Diel P, Olff S, Schmidt S, Michna H. 2001 Molecular identification of potential selective estrogen receptor modulator (serm) like properties of phytoestrogens in the human breast cancer cell line mcf-7. Planta Med. 67:510–4.

Glazier M G, Bowman M A. 2001. A review of the evidence for the use of phytoestrogens as a replacement for traditional estrogen replacement therapy. Arch Intern Med. 2001 161:1161–72.

Gustafsson J A, Warner M. 2000 Estrogen receptor beta in the breast: role in estrogen responsiveness and development of breast cancer. J Steroid Biochem Mol. Biol. 74:245–8.

Horvath L G, Henshall S M, Lee C S, Head D R, Quinn D I, Makela S, Delprado W, Golovsky D, Brenner P C, O'Neill G, Kooner R, Stricker P D, Grygiel J J, Gustafsson J A, Sutherland R L. 2001 Frequent loss of estrogen receptor-beta expression in prostate cancer. Cancer Res. 61:5331–5.

Kuroda M, Mimaki Y, Sashida Y, Umegaki E, Yamazaki M, Chiba K, Mohri T, Kitahara M, Yasuda A, Naoi N, Xu Z W, Li M R. 2000. Flavonol glycosides from Epimedium sagittatum and their neurite outgrowth activity on PC12 h cells. Planta Med. 66:575–7.

Kurzer M S, Xu X. 1997 Dietary phytoestrogens. Annu Rev Nutr. 17:353–81.

Lee H P, Gourley L, Duffy S W, Esteve J, Lee J, Day N E. 1991 Dietary effects on breast-cancer risk in Singapore. Lancet. 337:1197–200.

Lee M K, Choi Y J, Sung S H, Shin D I, Kim J W, Kim Y C. 1995 Antihepatotoxic activity of icariin, a major constituent of Epimedium koreanum. Planta Med. 61:523–6.

Liang H R, Siren H, Jyske P, Reikkola M L. 1997a Characterization of flavonoids in extracts from four species of Epimedium by micellar electrokinetic capillary chromatography with diode-array detection. J Chromatogr Sci. 35:117–25.

Liang H R, Vuorela P, Vuorela H, Hiltunen R. 1997b. Isolation and immunomodulatory effect of flavonol glycosides from Epimedium hunanense. Planta Med. 63:316–9.

Lindner V, Kim S K, Karas R H, Kuiper G G, Gustafsson J A, Mendelsohn M E. 1998 Increased expression of estrogen receptor-beta mRNA in male blood vessels after vascular injury. Circ Res. 83:224–9.

Milligan S R, Kalita J C, Heyerick A, Rong H, De Cooman L, De Keukeleire D. 1999 Identification of a potent phytoestrogen in hops (Humulus lupulus L.) and beer. J Clin Endocrinol Metab. 84:2249–52.

Omoto Y, Kobayashi Y, Nishida K, Tsuchiya E, Eguchi H, Nakagawa K, Ishikawa Y, Yamori T, Iwase H, Fujii Y, Warner M, Gustafsson J A, Hayashi S I. 2001. Expression, function, and clinical implications of the estrogen receptor beta in human lung cancers. Biochem Biophys Res Commun. 285:340–7.

Osterlund M K, Gustafsson J A, Keller E, Hurd Y L. 2000 Estrogen receptor beta (ERbeta) messenger ribonucleic acid (mRNA) expression within the human forebrain: distinct distribution pattern to ERalpha mRNA. J Clin Endocrinol Metab. 85:3840–6.

Paech K, Webb P, Kuiper G G, Nilsson S, Gustafsson J, Kushner P J, Scanlan T S. 1997 Differential ligand activation of estrogen receptors ERalpha and ERbeta at AP1 sites. Science. 277:1508–10.

Pettersson K, Gustafsson J A 2001. Role of estrogen receptor beta in estrogen action. Annu Rev Physiol. 63:165–92.

Pharmacopoeia of the Peoples Republic of China, 1997. Compiled by Pharmacopoeia Commission of PRC, English edition. Chemical Industry Press. Beijing, Vol I pg 93–94.

Pike A C, Brzozowski A M, Hubbard R E, Bonn T, Thorsell A G, Engstrom O, Ljunggren J, Gustafsson J A, Carlquist M. 1999 Structure of the ligand-binding domain of oestrogen receptor beta in the presence of a partial agonist and a full antagonist. EMBO J. 18:4608–18.

Roger P, Sahla ME, Makela S, Gustafsson JA, Baldet P, Rochefort H. 2001 Decreased expression of estrogen receptor beta protein in proliferative preinvasive mammary tumors. Cancer Res. 61:2537–41.

Rosenberg Zand R S, Jenkins D J A, Diamandis E P. 2000. Steroid hormone activity of flavonoids and related compounds. Breast cancer research and treatment 2000, 62, 35.

Setchell K D. 1998 Phytoestrogens: the biochemistry, physiology, and implications for human health of soy isoflavones. Am J Clin Nutr. 68(6 Suppl):1333S–1346S.

Tham D M, Gardner C D, Haskell W L 1998. Potential health benefits of dietary phytoestrogens: a review of the clinical, epidemiological, and mechanistic evidence. J Clin Endocrinol Metab. 83:2223–35.

Wang L, Andersson S, Warner M, Gustafsson J A. 2001. Morphological abnormalities in the brains of estrogen receptor beta knockout mice. Proc Natl Acad Sci USA. 98:2792–6.

Weihua Z, Makela S, Andersson L C, Salmi S, Saji S, Webster J I, Jensen E V, Nilsson S, Warner M, Gustafsson J A. 2001 A role for estrogen receptor beta in the regulation of growth of the ventral prostate. Proc Natl Acad Sci USA. 98:6330–5.

Zava D T, Dollbaum C M, Blen M. 1998 Estrogen and progestin bioactivity of foods, herbs, and spices. Proc Soc Exp Biol Med. 217:369–78.

U.S. Patents

U.S. Pat. No. 6,071,883: Chen H F. June 2000, Flavone analogues useful as anti-rejection agents.

U.S. Pat. No. 6,123,944: Chen Y J, September 2000. Icariin preparations.

U.S. Pat. No. 6,238,707: Chun Z, May 2001. Herbal hormone balance composition.

U.S. Pat. No. 5,874,084: Yng Wong February 1999. Using complex herbal formulations to treat hot flashes.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A compound having the formula:

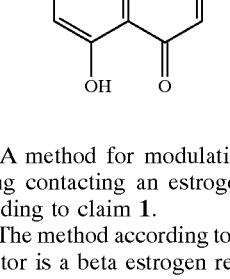

2. A method for modulating an estrogen receptor comprising contacting an estrogen receptor with a compound according to claim 1.

3. The method according to claim 2, wherein said estrogen receptor is a beta estrogen receptor (ER-beta).

4. The method according to claim 2, wherein said estrogen receptor is an alpha estrogen receptor (ER-alpha).

5. The method according to claim 2, wherein said estrogen receptor is a heterodimer consisting of an alpha estrogen receptor subunit and a beta estrogen receptor subunit (ER-alpha/ER-beta).

6. A pharmaceutical composition, nutritional supplement, food product or beverage, comprising a compound according to claim 1.

7. The pharmaceutical composition, nutritional supplement, food product or beverage according to claim 6, adapted for delivery of said compound in a daily dose of from about 0.3 µg/kg to about 20 mg/kg of body weight.

8. A commercial package comprising a pharmaceutical composition, nutritional supplement, food product or beverage according to claim 6 together with instructions for use for modulating an estrogen receptor.

9. A method for modulating an estrogen receptor comprising contacting said estrogen receptor with a compound having the formula:

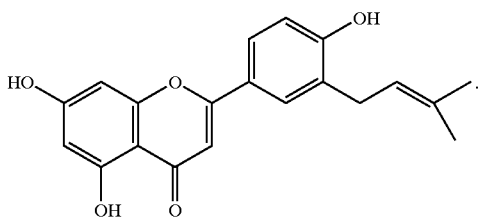

10. The method according to claim 9, wherein said estrogen receptor is a beta estrogen receptor (ER-beta).

11. The method according to claim 9, wherein said estrogen receptor is an alpha estrogen receptor (ER-alpha).

12. The method according to claim 9, wherein said estrogen receptor is a heterodimer consisting of an alpha estrogen receptor subunit and a beta estrogen receptor subunit (ER-alpha/ER-beta).

13. A compound having the formula:

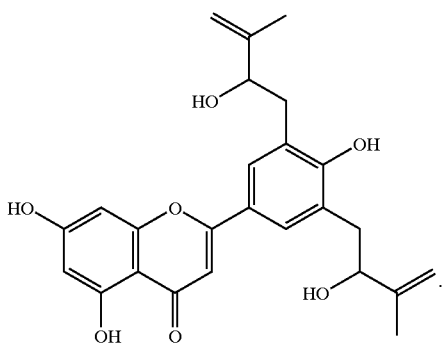

14. A method for preparing a preparation having estrogenic activity from a plant, said method comprising:

(a) extracting the plant or a part thereof with a solvent to obtain an extract;

(b) fractionating said extract to obtain a plurality of fractions;

(c) assaying estrogen receptor agonist activity in the fractions from (b); and (d) collecting a fraction from (c) that is enriched for estrogen receptor agonist activity by about 2-fold or more relative to said extract, wherein said fraction is enriched for a compound having the formula:

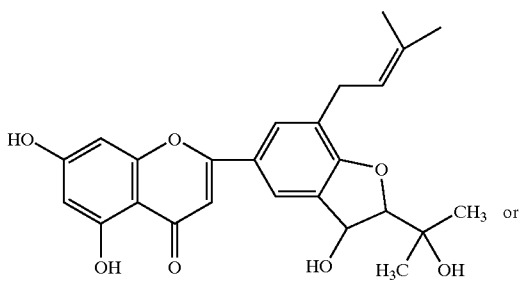

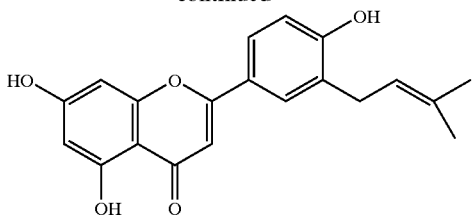

15. The method according to claim 14, wherein said fraction from (c) is enriched for estrogen receptor agonist activity by about 2-fold to about 6-fold relative to said crude extract solvent comprises at least about 10% to about 100% alcohol.

16. The method according to claim 14, wherein said solvent comprises at least about 10% to about 100% alcohol.

17. The method according to claim 14, wherein said solvent comprises about 95% to about 100% ethanol.

18. The method according to claim 14, wherein said estrogenic activity is selective for alpha estrogen receptors (ER-alpha) over beta estrogen receptors (ER-beta).

19. The method according to claim 14, wherein said estrogenic activity is selective for beta estrogen receptors (ER-beta) over alpha estrogen receptors (ER-alpha).

20. The method according to claim 14, wherein said fractionating comprises a first fractionating process comprising: loading said extract onto a first chromatography column; eluting said first chromatography column with a first solvent gradient of increasing or decreasing polarity; and collecting a plurality of first fractions.

21. The method according to claim 20, further comprising a second fractionating process comprising: loading one or more of said first fractions onto a second chromatography column; eluting said second chromatography column with a second solvent gradient of increasing or decreasing polarity; and collecting a plurality of second fractions.

22. The method according to claim 21, wherein said second chromatography column is an HPLC column.

23. The method according to claim 21, further comprising a third fractionating process comprising: loading one or more of said second fractions onto a third chromatography column; eluting said third chromatography column with a third solvent gradient of increasing or decreasing polarity; and collecting a plurality of third fractions.

24. The method according to claim 23, wherein said third chromatography column is an HPLC column.

25. The method according to claim 14, wherein said plant is an Epimedium plant of a species selected from the group consisting of: *Epimedium sagittatum, Epimedium koreanum, Epimedium brevicornum, Epimedium pubescens, Epimedium wushanense, Epimedium grandiflorum, Epimedium hunanense, Epimedium acuminatum, Epimedium dividi, Epimedium fargesii, Epimedium baicaliquizhounense, Epimedium sutchuenences, Epimedium caotum, Epimedium glandolospilosum, Epimedium zushanense, Epimedium reticulatum, Epimedium baojingenensis, Epimedium simplicifolium, Epimedium clongatum, Epimedium ecalcaratum, Epimedium truncatum, Epimedium haiyangense* and *Epimedium platypetalum.*

26. The method according to claim 14, wherein said plant is an Epimedium species selected from the group consisting of *Epimedium brevicornum* Maxis, *Epimedium sagittatum* (Sieb. Et Zucc.) Maxim, *Epimedium pubescens* Maxim, *Epimedium wushanense* T. S. Ying, and *Epimedium koreaneum* Nakai (Fam. Berberidaceae).

27. The method according to claim 14, wherein said fraction from (d) is enriched for a compound having the formula:

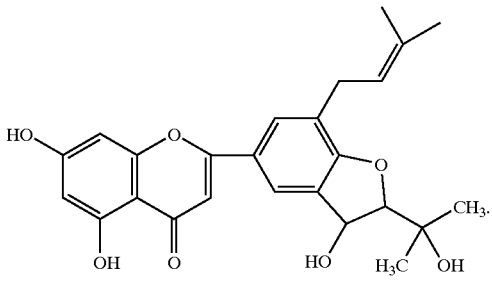

28. The method according to claim 14, wherein said fraction from (d) is enriched for a compound having the formula:

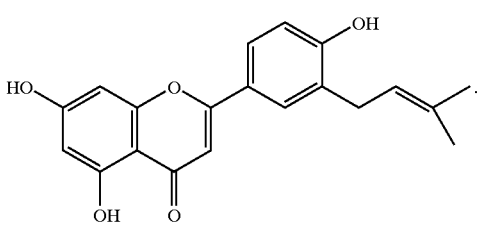

29. The method according to claim 14, wherein said plant is selected from the group consisting of *Amenarrhena asphodeloides, Dioscorea opposita, Cuscuta chinensis,* and *Psoralea corylifoloa.*

30. A preparation prepared according to the method of claim 29.

31. A preparation having estrogenic activity obtained from an Epimedium plant, wherein said preparation comprises between about 0.002% to 99.9% by weight of a compound having the formula:

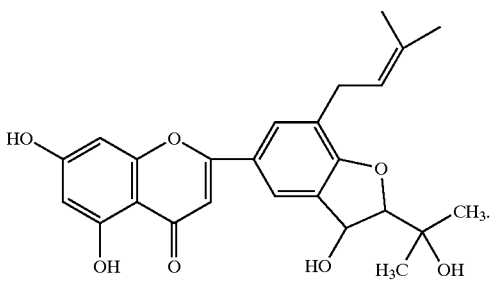

32. The preparation according to claim 31, wherein said preparation activates beta estrogen receptors (ER-beta) more strongly than alpha estrogen receptors (ER-alpha) by about 2-fold to 9-fold.

33. A pharmaceutical composition, nutritional supplement, food product or beverage, comprising a preparation according to claim 31.

34. The pharmaceutical composition, nutritional supplement, food product or beverage according to claim 33, adapted for delivery of said compound in a daily dose of from about 0.3 µg/kg to about 20 mg/kg body weight.

35. The pharmaceutical composition, nutritional supplement, food product or beverage according to claim 33, in a form adapted for oral administration.

36. A commercial package comprising a preparation according to claim 31 together with instructions for use for modulating an estrogen receptor.

37. A method for preventing or treating a condition mediated by an estrogen receptor in a subject comprising administering to a subject in need thereof a therapeutically effective amount of:

(i) a compound of the formula:

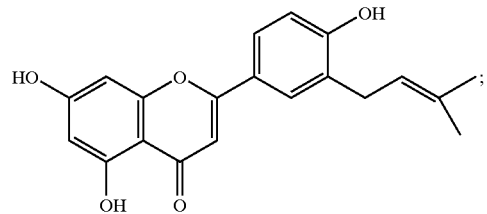

(ii) a compound of the formula:

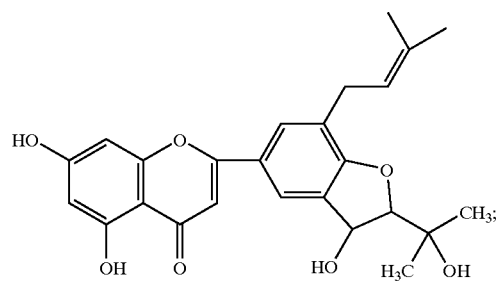

(iii) a mixture of said compound in (i) and said compound in (ii); or (iv) a preparation having estrogenic activity obtained from an Epimedium plant, wherein said preparation comprises between about 0.002% to 99.9% of a compound of the formula:

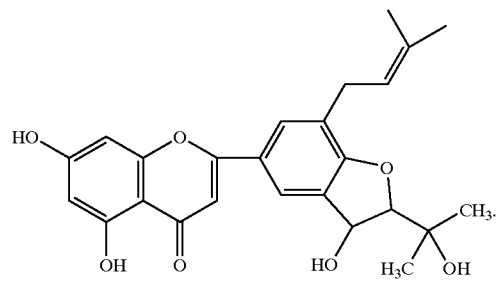

38. The method according to claim 37, wherein said compound is administered in a daily dose of from about 0.3 µg/kg to about 20 mg/kg of body weight.

39. The method according to claim 37, wherein said condition mediated by an estrogen receptor condition is selected from the group consisting of: premature ovarian failure; menopause; post-menopause; osteoporosis; menstrual irregularities; hot flushes; genital tract atrophy; lack of libido; depression; abnormalities of lipid metabolism; cardiovascular disease; cerebrovascular disease; atherosclerosis; coronary artery disease; stroke; and cancer.

40. The method according to claim 37, wherein said condition mediated by an estrogen receptor is menopause or post-menopause.

41. The method according to claim 37, wherein said condition is mediated by a beta estrogen receptor (ER-beta) subtype and said compound in (ii) or said preparation in (iv) is administered.

42. The method according to claim 41, wherein said condition mediated by an estrogen receptor is selected from the group of conditions consisting of: premature ovarian failure; menopause; post-menopause; osteoporosis; menstrual irregularities; hot flushes; genital tract atrophy; lack of libido; depression; abnormalities of lipid metabolism; cardiovascular diseases; disorders of the cardiovascular system; cerebrovascular diseases; atherosclerosis; coronary artery disease; strokes; degenerative disorders of the nervous system; disorders of the nervous system resulting from trauma or stroke; prostatic hyperplasia; cancer; male infertility; female infertility.

43. The method according to claim 42, wherein the degenerative disorder of the nervous system is Alzheimer's or Parkinson's disease.

44. The method according to claim 42, wherein said cancer is prostate carcinoma, breast carcinoma, or endometrial carcinoma.

45. The method according to claim 42, wherein the disorder of the cardiovascular system is stroke or coronary arterial disease.

46. The method according to claim 41, wherein said condition mediated by an estrogen receptor is menopause or post-menopause.

47. The method according to claim 37, wherein said compound in (i) is administered.

48. The method according to claim 37, wherein said mixture in (iii) is administered.

49. A commercial package comprising a pharmaceutical composition comprising a preparation according to claim 31, and instructions for use of said composition for treating a condition mediated by an estrogen receptor in a subject.

50. The commercial package according to claim 49, wherein said condition mediated by an estrogen receptor is menopause or post-menopause.

51. The commercial package according to claim 49, wherein said estrogen receptor is a beta estrogen receptor (ER-beta).

* * * * *

UNITED STATES PATENT AND TRADEMARK OFFICE
CERTIFICATE OF CORRECTION

PATENT NO. : 6,750,248 B2
DATED : June 15, 2004
INVENTOR(S) : Eu L. Yong et al.

It is certified that error appears in the above-identified patent and that said Letters Patent is hereby corrected as shown below:

Title page,
Item [56], References Cited, OTHER PUBLICATIONS,
"Österlund" reference, please add -- Metabolism vol. 85(10): pp. 3840-3846 --
"Chemical Abstract 86" reference, please delete "Metabolite vol. 85(10): pp. 3840-3846"

Column 30,
Line 15, please delete "...solvent comprises at least about 10% to about 100% alcohol."
Line 54, "...dividi ..." should be -- ...dividii... --

Signed and Sealed this

Twelfth Day of April, 2005

JON W. DUDAS
*Director of the United States Patent and Trademark Office*